(12) United States Patent
Bencke et al.

(10) Patent No.: US 10,850,059 B2
(45) Date of Patent: Dec. 1, 2020

(54) FLUID CONNECTOR WITH FACE SEAL

(71) Applicant: ResMed Pty Ltd, Bella Vista (AU)

(72) Inventors: James McKensey Bencke, Sydney (AU); Justin John Formica, Sydney (AU); Richard Llewelyn Jones, Hornsby Heights (AU); Joseph Samuel Ormrod, Sydney (AU); Mark Simpson, Sydney (AU); Jamie Graeme Wehbeh, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 470 days.

(21) Appl. No.: 15/556,781

(22) PCT Filed: Mar. 8, 2016

(86) PCT No.: PCT/AU2016/050162
§ 371 (c)(1),
(2) Date: Sep. 8, 2017

(87) PCT Pub. No.: WO2016/141430
PCT Pub. Date: Sep. 15, 2016

(65) Prior Publication Data
US 2018/0043125 A1  Feb. 15, 2018

Related U.S. Application Data

(60) Provisional application No. 62/281,773, filed on Jan. 22, 2016, provisional application No. 62/130,813, filed on Mar. 10, 2015.

(51) Int. Cl.
*A61M 16/00* (2006.01)
*F16L 37/086* (2006.01)
(Continued)

(52) U.S. Cl.
CPC ........ *A61M 16/0816* (2013.01); *A61M 39/10* (2013.01); *F16L 37/086* (2013.01);
(Continued)

(58) Field of Classification Search
CPC .. A61M 16/0186; A61M 39/10; A61M 16/08; A61M 16/0875
(Continued)

(56) References Cited

U.S. PATENT DOCUMENTS 2,939,729 A   6/1960  O'Shaughnessy, Jr.
3,439,944 A   4/1969  Leutenegger
(Continued)

FOREIGN PATENT DOCUMENTS

CN   101951984 A   1/2011
CN   103252008 A   8/2013
(Continued)

OTHER PUBLICATIONS

Jan. 3, 2019 Office Action issued in Chinese Application No. 201680013439.5 (with English-language translation).
(Continued)

*Primary Examiner* — Bradley H Philips
*Assistant Examiner* — Savannah L Gabriel
(74) *Attorney, Agent, or Firm* — Nixon & Vanderhye P.C.

(57) ABSTRACT

One form of the present technology includes a fluid connector for delivery of breathing gas to a patient from a respiratory pressure therapy device, the fluid connector including a first end with a first opening to deliver a fluid flow, a seal portion extending around a periphery of the first opening, and a latching portion, a second end with a second opening to receive the fluid flow, a sealing surface extending around a periphery of the second opening and configured to
(Continued)

engage the seal portion to form a face seal, and a complementary latching portion configured to engage with the latching portion.

24 Claims, 25 Drawing Sheets

(51) Int. Cl.
*A61M 16/08* (2006.01)
*A61M 39/10* (2006.01)
*F16L 37/098* (2006.01)

(52) U.S. Cl.
CPC ........ *F16L 37/098* (2013.01); *A61M 16/0066* (2013.01); *A61M 2016/0027* (2013.01); *A61M 2016/0033* (2013.01); *A61M 2205/276* (2013.01); *A61M 2205/42* (2013.01); *A61M 2205/6045* (2013.01)

(58) Field of Classification Search
USPC .............................. 128/202.27; 285/319, 352
See application file for complete search history.

(56) References Cited

U.S. PATENT DOCUMENTS

| | | | |
|---|---|---|---|
| 3,826,523 | A | 7/1974 | Eschbaugh |
| 4,305,606 | A | 12/1981 | Legris |
| 4,541,658 | A | 9/1985 | Bartholomew |
| 4,782,832 | A | 11/1988 | Trimble et al. |
| 4,941,689 | A | 7/1990 | Sjöberg |
| 4,944,310 | A | 7/1990 | Sullivan |
| 5,078,429 | A * | 1/1992 | Braut ................ F16L 37/38 285/4 |
| 6,532,959 | B1 | 3/2003 | Berthon-Jones |
| 6,581,594 | B1 | 6/2003 | Drew et al. |
| 7,866,944 | B2 | 1/2011 | Kenyon et al. |
| 8,002,313 | B2 | 8/2011 | Singh et al. |
| 8,490,622 | B2 | 7/2013 | Stenzler et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 8,770,190 | B2 | 7/2014 | Doherty et al. |
| 2003/0106600 | A1* | 6/2003 | Ohlendorf ............... A47L 9/242 138/96 R |
| 2007/0169825 | A1 | 7/2007 | Packham et al. |
| 2008/0041391 | A1 | 2/2008 | Worley |
| 2008/0264413 | A1 | 10/2008 | Doherty et al. |
| 2009/0044808 | A1 | 2/2009 | Guney et al. |
| 2009/0050156 | A1 | 2/2009 | Ng et al. |
| 2009/0260629 | A1 | 10/2009 | Yee et al. |
| 2010/0000534 | A1 | 1/2010 | Kooij et al. |
| 2010/0116272 | A1 | 5/2010 | Row et al. |
| 2011/0023874 | A1 | 2/2011 | Bath et al. |
| 2012/0272954 | A1 | 11/2012 | Landis et al. |
| 2013/0167841 | A1* | 7/2013 | Sheffer ............. A61M 16/0816 128/202.27 |
| 2014/0202460 | A1 | 7/2014 | Bath et al. |

FOREIGN PATENT DOCUMENTS

| | | |
|---|---|---|
| EP | 1 369 141 A1 | 12/2003 |
| JP | 0328494 | 8/1989 |
| JP | 1-223922 | 9/1989 |
| WO | WO 98/004310 A1 | 2/1998 |
| WO | WO 98/034665 A1 | 8/1998 |
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | WO 2012/171072 A1 | 12/2012 |
| WO | WO 2013/020167 A1 | 2/2013 |
| WO | WO 2013/132086 A1 | 9/2013 |
| WO | WO 2014/097068 A1 | 6/2014 |
| WO | WO 2017/006189 A1 | 1/2017 |

OTHER PUBLICATIONS

Oct. 17, 2018 Extended European Search Report issued in European Application No. 16760933.8.
International Search Report for PCT/AU2016/050162, mailed.
Written Opinion of the ISA for PCT/AU2016/050162, mailed.
"*Respiratory Physiology*", by John B. West, Lippincott Williams & Wilkins, 9th edition published 2012 (8 pages).
Office Action issued in Japanese Application No. 2017-545958 dated Jun. 1, 2020 with English translation (20 pages).

* cited by examiner

FLUID CONNECTOR WITH FACE SEAL

This application is the U.S. national phase of International Application No. PCT/AU2016/050162 filed Mar. 8, 2016, which designated the U.S. and claims the benefit of U.S. Provisional Application No. 62/130,813, filed Mar. 10, 2015, and U.S. Provisional Application No. 62/281,773, filed Jan. 22, 2016, the entire contents of each of which are incorporated herein by reference in its entirety.

1 BACKGROUND OF THE TECHNOLOGY

1.1 Field of the Technology

The present technology relates to one or more of the detection, diagnosis, treatment, prevention and amelioration of respiratory-related disorders. The present technology also relates to medical devices or apparatus, and their use. The present technology also relates to a fluid connector for use such medical devices or apparatus.

1.2 Description of the Related Art

1.2.1 Human Respiratory System and its Disorders

The respiratory system of the body facilitates gas exchange. The nose and mouth form the entrance to the airways of a patient.

A range of respiratory disorders exist. Certain disorders may be characterised by particular events, e.g. apneas, hypopneas, and hyperpneas.

A range of therapies have been used to treat or ameliorate conditions such as Obstructive Sleep Apnea (OSA), Cheyne-Stokes Respiration (CSR), Obesity Hyperventilation Syndrome (OHS), Chronic Obstructive Pulmonary Disease (COPD), Neuromuscular Disease (NMD) or chest wall disorders. Furthermore, otherwise healthy individuals may take advantage of such therapies to prevent respiratory disorders from arising. However, these have a number of shortcomings.

1.2.2 Therapy

Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient in taking a full breath and/or maintain adequate oxygen levels in the body by doing some or all of the work of breathing. The ventilatory support is provided via a patient interface. NIV has been used to treat CSR, OHS, COPD, MD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

1.2.2.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

Patient interfaces may include a seal-forming portion. A patient interface may be partly characterised according to the design intent of where the seal-forming portion is to engage with the face in use. These different types of patient interfaces may be known by a variety of names by their manufacturer including nasal masks, full-face masks, nasal pillows, nasal puffs and oro-nasal masks.

1.2.2.1.1 Vent Technologies

Some forms of treatment systems may include a vent to allow the washout of exhaled carbon dioxide, such as in a patient interface. The vent may allow a flow of gas from an interior space of the patient interface, e.g., the plenum chamber, to an exterior of the patient interface, e.g., to ambient. The vent may comprise an orifice and gas may flow through the orifice in use of the mask. Many such vents are noisy. Others may become blocked in use and thus provide insufficient washout. Some vents may be disruptive of the sleep of a bed-partner 1100 of the patient 1000, e.g. through noise or focussed airflow.

1.2.2.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO3744 in CPAP mode at 10 $cmH_2O$).

| RPT Device name | A-weighted sound power level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator.

RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

1.2.2.3 Humidifier

Delivery of a flow of air without humidification may cause drying of airways. The use of a humidifier with an RPT device and the patient interface produces humidified gas that minimizes drying of the nasal mucosa and increases patient airway comfort.

Medical humidifiers are used to increase humidity and/or temperature of the flow of air in relation to ambient air when required, typically where the patient may be asleep or resting (e.g. at a hospital).

1.2.3 Diagnosis and Treatment Systems

These therapies may be provided by a treatment system or device. Systems and devices may also be used to diagnose a condition without treating it.

CPAP therapy is highly effective to treat certain respiratory disorders, provided patients comply with therapy.

A treatment system may comprise a Respiratory Pressure Therapy Device (RPT device), an air circuit, a humidifier, a patient interface, and data management.

One component of a treatment system may be connectable to another component to the system via an industry standard connector. For example, a patient interface may be connectable to an air circuit by a connector defined in ISO 5356-1. In such configurations, however, it may be difficult to determine whether a component is designed such that its optimal use condition is with another component. As a result, a user may not be able to take full advantage of treatment systems wherein components, such as an RPT device, may be specifically designed for use with a particular set of patient interfaces for example.

Furthermore, adoption of a standard connector in a component may constrain the designer, in that the designer must ensure that the component is compatible with all other components connectable via the standard connector. Thus, the designer may be discouraged, or even prevented from making improvements to the component if it may not be backwards compatible with the existing suite of connectable component in the market.

If, indeed, a bespoke connector is used, it is preferably arranged such that accidental, or unintended, connection between a component utilising a bespoke connector and a component utilising another connector can be prevented.

Still further, existing connectors themselves may not be desirable in one or more aspects. For example, a connector engageable purely by interference fit (e.g. as defined in ISO 5356-1) may be difficult to engage and/or disengage as it may require a large force to overcome the friction across a length of the connection. Such a connector may further not provide a clear indication to the user whether the connection has been adequately made or not for provision of therapy.

Thus, a need exists for an improved connector, which is identifiably different from other connectors, and preferably prevents unintended connection to components that utilise standard connectors. Such an improved connector may enable development an improved treatment system comprising components that are designed for use with each other. In turn, improved therapy may be delivered to the patient, as well as achieving an increased rate of compliance with the therapy.

2 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

A first form of the present technology includes a connector set with a compliant face seal between a first end and a second end of the connector set and with a retention mechanism that couples the first end and the second end together.

A second form of the present technology comprises a fluid connector system for delivery of breathing gas to a patient from a respiratory pressure therapy device, the fluid connector system comprising a first end with a first opening for a fluid flow, a seal portion extending around a periphery of the first opening, and a latching portion, and a second end with an inner tube defining a second opening for the fluid flow, a sealing surface extending around a periphery of the second opening and configured to engage the seal portion to form a face seal, and an outer tube comprising a complementary latching portion configured to engage with the latching portion and configured to be depressed into a cavity formed between the inner tube and the outer tube, wherein the face seal forms a seal to breathing gas travelling between the first opening and the second opening, and the engagement between the latching portion and the complementary latching portion secures the first end with the second end.

A third form of the present technology comprises a system for providing respiratory therapy to a patient, the system comprising a respiratory pressure therapy device; an air circuit; a patient interface connected to the air circuit and a means for preventing the respiratory pressure therapy device from being connected to the air circuit with an industry standard connection.

A fourth form of the present technology comprises a method of providing a fluid connection to deliver breathing gas to a patient from a respiratory pressure therapy device, the method comprising engaging a latch between a first end and a second end of the fluid connection; and engaging a face seal around a first opening in the first end and around a second opening in the second end, wherein one of the first end and the second end corresponds to the respiratory pressure therapy device.

A fifth form of the present technology comprises a first part of a fluid connector system for delivery of breathing gas to a patient from a respiratory pressure therapy device, the first part comprising connector portion with a first opening for a fluid flow, a seal portion extending around a periphery of the first opening, and a latching portion, wherein the seal portion is configured to seal against a sealing surface extending around a periphery of a second opening to form a face seal with a second part of the fluid connector system, and the latching portion is configured to latch with another latching portion of the second part of the fluid connector system.

A sixth form of the present technology comprises a first part of a fluid connector system for delivery of breathing gas to a patient from a respiratory pressure therapy device, the first part comprising a connector portion with a first opening for a fluid flow, a sealing surface around a periphery of the first opening, and a latching portion, wherein the sealing surface is configured to receive a seal portion extending around a periphery of a second opening to form a face seal with a second part of the fluid connector system, and the latching portion is configured to latch with another latching portion of the second part of the fluid connector system.

A seventh form of the present technology comprises a fluid connector system for delivery of breathing gas to a patient from a respiratory pressure therapy device, the fluid connector system comprising a first end with a first interior portion for a fluid flow and a first retaining portion, and a second end with a second interior portion for the fluid flow and a complementary retaining portion configured to engage with the retaining portion, wherein the first interior portion and the second interior portion have a first shape in a plane perpendicular to a flow direction, the retaining portion and the complementary retaining portion have a second shape in a plane perpendicular to the flow direction, and the first shape and the second shape are different.

An eighth form of the present technology comprises a system for providing respiratory therapy to a patient, the system comprising a respiratory pressure therapy device; an air circuit; a patient interface connected to the air circuit, the patient interface being adapted to operate with the respiratory pressure therapy device; and a means for ensuring that the patient interface that is adapted to operate with the respiratory pressure therapy device is able to connect to the respiratory pressure therapy device to receive a delivery of breathable gas therefrom while patient interfaces not adapted to operate with the respiratory pressure therapy device are not able to connect to the respiratory pressure therapy device to receive a delivery of breathable gas therefrom.

A ninth form of the present technology comprises a fluid connector end for delivering a flow of pressurised air for respiratory therapy to a patient, the fluid connector end comprising: an outer portion comprising a latching portion and an overhang portion, the latching portion comprising a protrusion configured to engage with a complementary recess; and an inner portion comprising a sealing surface, the inner portion defining an air path for delivering the flow of pressurised air, wherein the sealing surface comprises an annular surface for making a face seal to deliver the flow of pressurised air to the air path, and the protrusion is located axially in line with the sealing surface.

In examples of at least one of the first through ninth forms of the present technology, (a) the second end further comprises a stabiliser located between the inner tube and the outer tube; (b) the stabiliser is formed at least in part from an elastomer; (c) the first end is connected to a respiratory pressure therapy device including a blower and the second end is connected to a fluid conduit; (d) the sealing surface is flat; (e) the sealing surface is substantially perpendicular to a direction of the fluid flow from the first end to the second end; (f) the sealing surface extends circumferentially around the second opening; (g) the sealing surface is formed on a flange that extends radially from the inner tube; (h) the flange extends substantially perpendicularly from the inner tube; (i) the inner tube extends beyond the flange in a direction towards the seal portion; (j) the inner tube extends at least partially though the seal portion when the complementary latching portion is engaged with the latching portion; (k) the seal portion is compliant in a direction of engagement between the first end and the second end; (l) the seal portion includes a frustoconical portion; (m) the frustoconical portion contacts the sealing surface to form the face seal when the first end and the second end are connected; (n) the seal portion includes a partial spherical surface; (o) the partial spherical surface contacts the sealing surface to form the face seal when the first end and the second end are connected; (p) the seal portion includes a bellows-shaped or partial bellows-shaped portion; (q) the bellows-shaped or partial bellows-shaped portion contacts the sealing surface to form the face seal when the first end and the second end are connected; (r) when the first end and the second end are connected the seal portion is configured to engage the sealing surface before the latching portion and the complementary latching portion engage; (s) the seal portion is compliant in a direction radial to an axis defined by a direction of engagement between the first end and the second end; (t) the seal portion is configured to expand and engage the sealing surface due to internal pressurization of the first end when a gap exists between the seal portion and the sealing surface in an unpressurized state; (u) contact between the seal portion and the sealing surface causes the seal portion to compress against the sealing and against an airflow direction that is from the first opening to the second opening; (v) compression of the seal portion does not cause significant compressive forces; (w) a force required to compress the seal portion is less than a force required to engage the latching portion with the complementary latching portion; (x) the force required to compress the seal portion is less than half of the force required to engage the latching portion with the complementary latching portion; (y) the force required to compress the seal portion is less than one tenth of the force required to engage the latching portion with the complementary latching portion; (z) at least one of the seal portion and the sealing surface includes sufficient contact area between the seal portion and the sealing surface to form a seal when respective centers of the seal portion and the sealing surface are not aligned with one another; (aa) the second end comprises an inner portion and an outer portion and the inner portion is rotatably coupled to the outer portion; (bb) the inner portion comprises the sealing surface; (cc) the inner portion is rigidly connected to a fluid conduit; (dd) the outer portion comprises the complementary latching portion; (ee) the complementary latching portion comprises a cantilevered portion with a protrusion that is configured to engage the latching portion; (ff) the cantilevered portion is configured to be depressed to engage or disengage the complementary latching portion from the latching portion and allow engagement or disengagement between the first end and the second end; (gg) the first end comprises a travel limit to constrain the second end from moving in a direction of engagement between the first end and the second end; (hh) the travel limit is a flange around the first opening and the second end comprises a stop surface configured to contact the flange; (ii) the latching portion constrains the second end from moving in a direction opposite to the direction of engagement, and the travel limit and latching portion together define a movement distance of the second end when the first end and the second end are engaged; (jj) the seal portion is configured to seal against the sealing surface throughout the movement distance, the movement distance being a non-zero distance; (kk) the seal portion is configured to form a seal with the sealing surface with a worst case manufacturing tolerance and after a predetermined amount of wear and/or creep in the fluid connector; (ll) the fluid connector system is configured to provide negligible pressure drop when air is flowing through the fluid connector system throughout a patient's breathing cycle and at pressures between 4 cm $H_2O$ to 40 cm $H_2O$; (mm) the first end is a female connection and the second end is a male connection; (nn) the female connection and the male connection have profiles that are non-circular; (oo) the first end includes a port in fluid communication with an interior of the seal portion and separated from the first opening and the second opening; (pp) the first opening and the second opening are interior portions of tubes; (qq) the first end is connected to a respiratory pressure therapy device including a blower and the second end is connected to an adapter for a fluid conduit connector; (rr) the fluid connector further comprises an industry standard fluid connection, wherein the industry standard fluid connection is in fluid communication with the first opening and on an end opposite the seal portion; (ss) the respiratory pressure therapy device comprises a first part of a fluid connector system and the air circuit comprises a second part of the fluid connector system, the first and second parts of the fluid connector system connecting together to connect the patient interface to the air circuit, and wherein one of the first part and second part comprises a non-circular male part and the other of the first part and second part comprises a non-circular female part, the non-circular male part being configured to mate with the non-circular female part when the first and second parts are connected; (tt) the first part comprises the male part and the second part comprises the female part; (uu) the first and second parts are able to be connected together in a plurality of mating orientations; (vv) the first and second parts are able to be connected together in two mating orientations; (ww) the male and female parts each comprise at least one flat portion and at least one curved portion in a plane perpendicular to a direction of air flow from the respiratory pressure therapy device to the air circuit; (xx) the male and female parts each comprise two opposing flat portions and two opposing curved portions in a plane perpendicular to a direction of air flow from the respiratory pressure therapy device to the air circuit; (yy) one of the male and female parts comprises at least one key and the other of the male and female parts comprises at least one slot, the at least one key being configured to mate with the at least one slot when the male part mates with the female part; (zz) the fluid connector further comprises an industry standard fluid connection, wherein the industry standard fluid connection is in fluid communication with the first opening and on an end opposite the sealing surface; (aaa) the first shape is a circle; (bbb) the second shape includes properties of a circle and a square; (ccc) the second shape comprises two opposing flat portions and two opposing curved portions; (ddd) one of the first interior portion and the second interior portion includes a first male portion and the other of the first interior portion and the second interior portion includes a first female portion, the first male portion and the first female portion including the first shape, and one of the retaining portion and the complementary retaining portion includes a second male portion and the other of the retaining portion and the complementary retaining portion includes a second female portion, the second male portion and the second female portion including the second shape; (eee) the inner portion further comprises a radial outer surface configured to limit radial deflection of the latching portion; (fff) the radial outer surface is axially in line with the sealing surface; (ggg) the outer portion further comprises a slot; and/or (iii) the slot is an elongate shape.

An aspect of one form of the present technology is a portable RPT device, including a fluid connector, that may be carried by a person, e.g., around the home of the person.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

3 BRIEF DESCRIPTION OF THE DRAWINGS

The present technology is illustrated by way of example, and not by way of limitation, in the figures of the accompanying drawings, in which like reference numerals refer to similar elements including:

3.1 Treatment Systems

FIG. 1A shows a system including a patient 1000 wearing a patient interface 3000, in the form of a nasal pillows, receiving a supply of air at positive pressure from an RPT device 4000. Air from the RPT device is humidified in a humidifier 5000, and passes along an air circuit 4170 to the patient 1000. A bed partner 1100 is also shown.

3.2 Respiratory System and Facial Anatomy

FIG. 2A shows an overview of a human respiratory system including the nasal and oral cavities, the larynx, vocal folds, oesophagus, trachea, bronchus, lung, alveolar sacs, heart and diaphragm.

3.3 Patient Interface

FIG. 3A shows a patient interface in the form of a nasal mask in accordance with one form of the present technology.

3.4 RPT Device

3.5 Humidifier

Figure 5A:
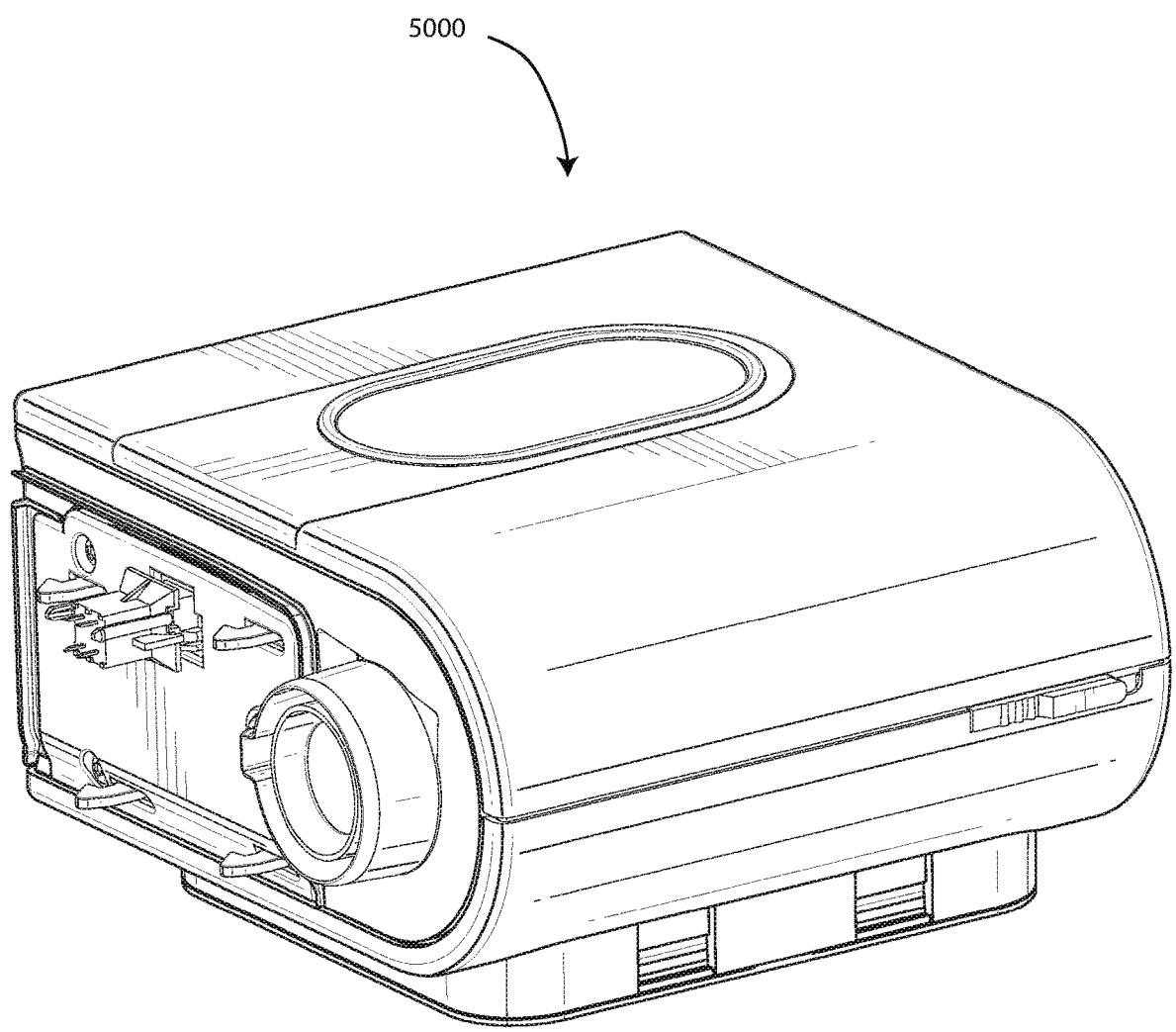

FIG. 5A shows an isometric view of a humidifier in accordance with one form of the present technology.

3.6 Fluid Connector

Figure 6A:
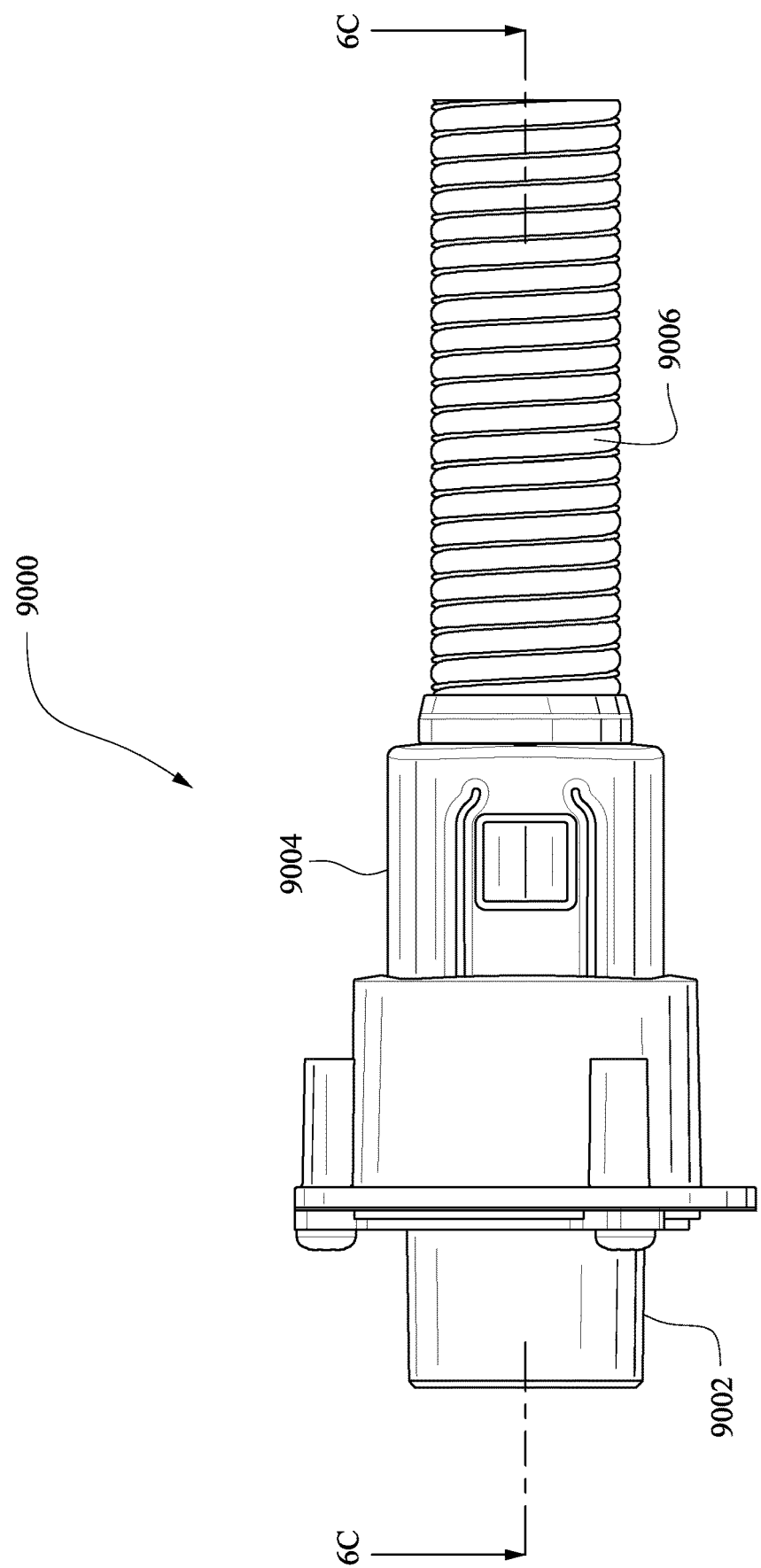

FIG. 6A shows a side view of a fluid connector with a first end and a second end mated with one another.

Figure 6B:
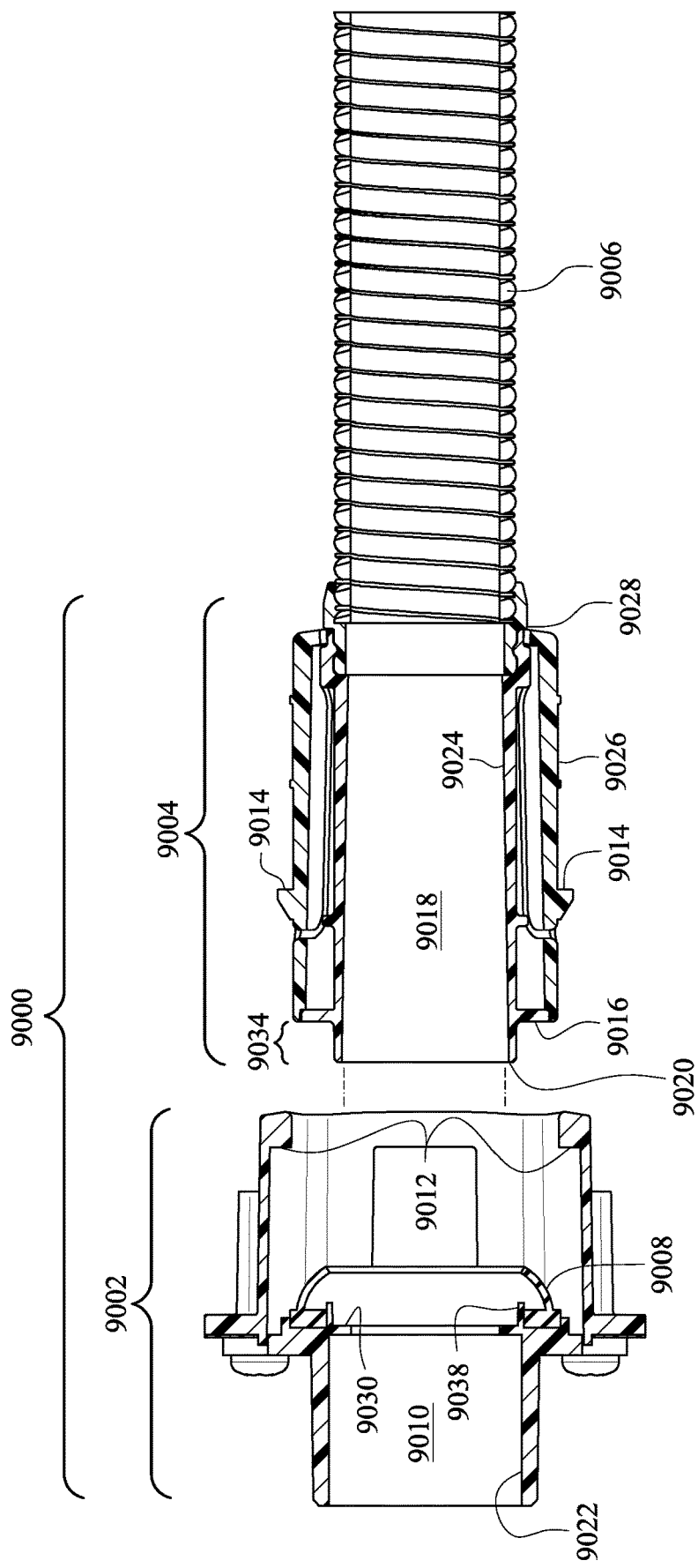

FIG. 6B shows a side, cross-sectional view of a fluid connector with a first end and a second end disengaged from one another.

Figure 6C:
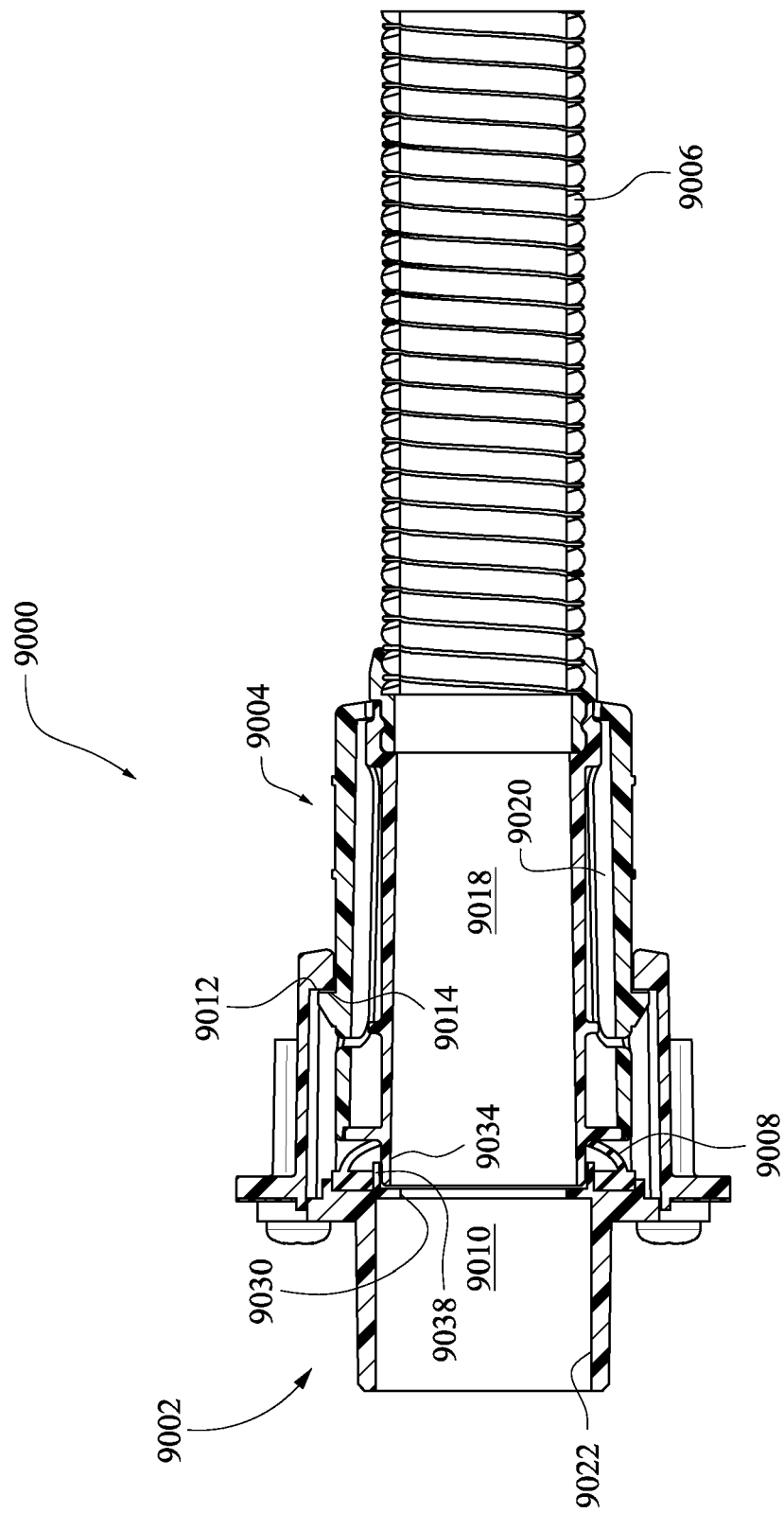

FIG. 6C shows a side, cross-sectional view of a fluid connector with a first end and a second end mated with one another.

Figure 6D:
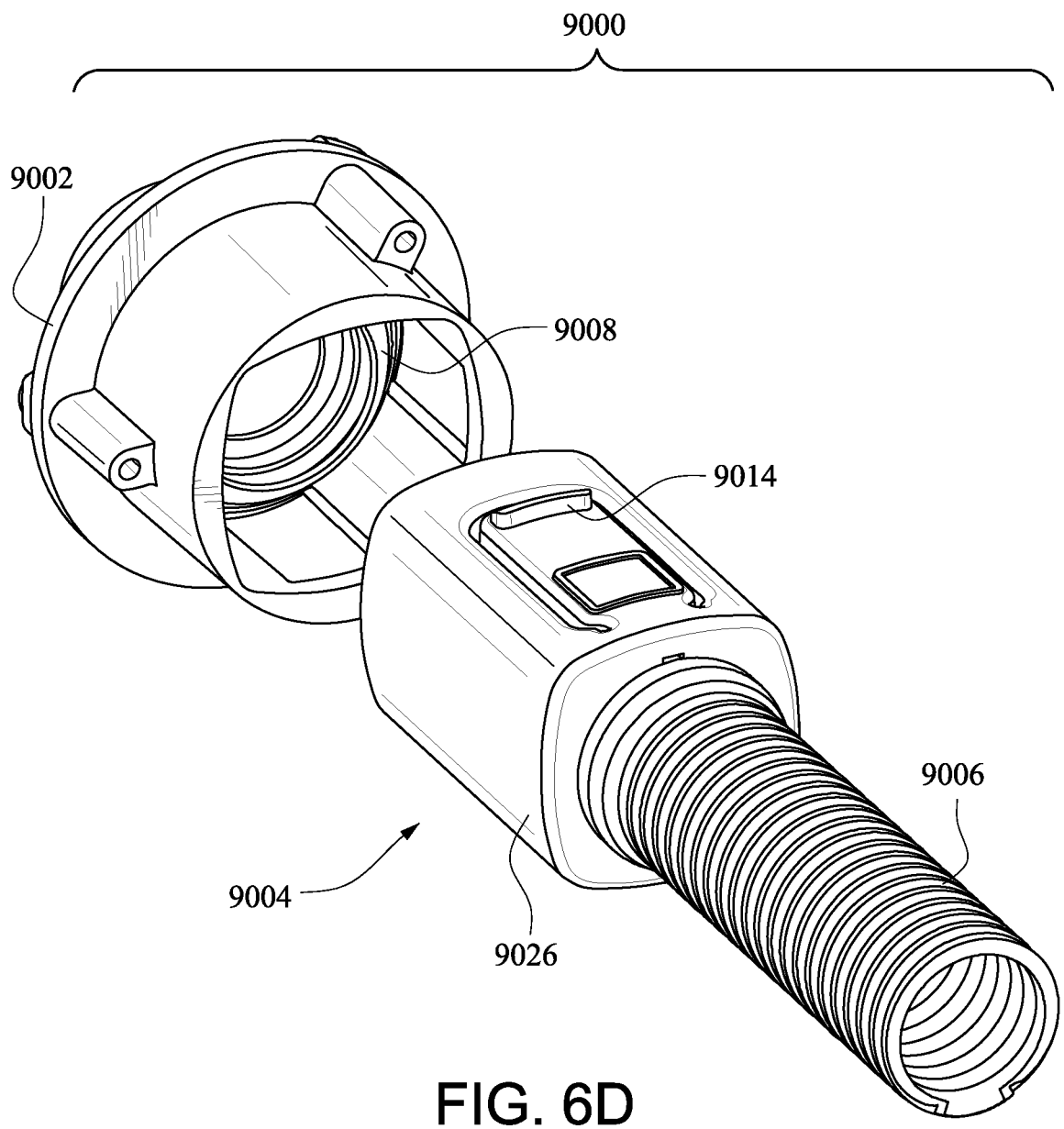

FIG. 6D shows a perspective view of a fluid connector with a first end and a second end separated from one another with an interior of the first end being visible.

Figure 6E:
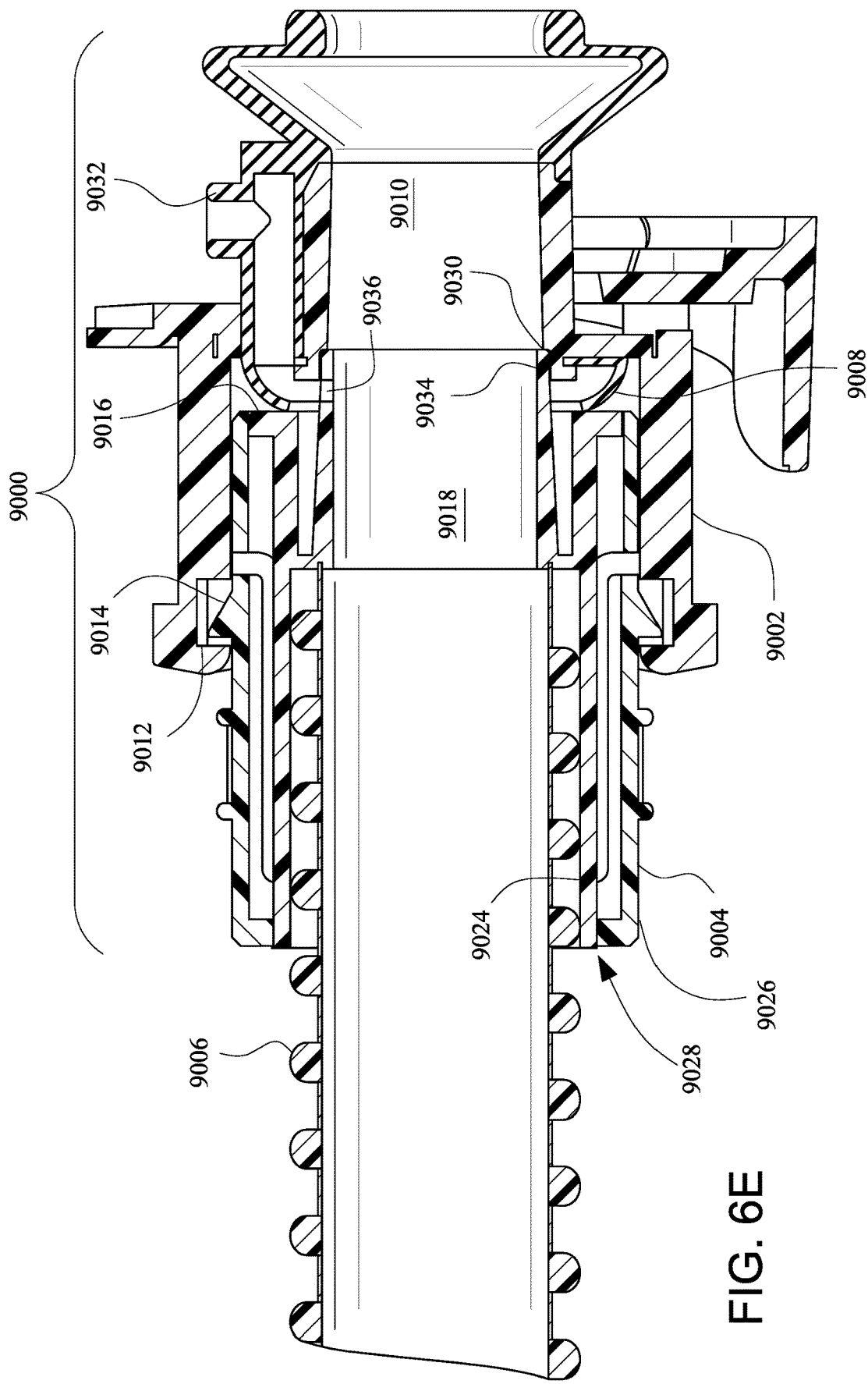

FIG. 6E shows a cross-sectional view of a fluid connector with an additional fluid port.

Figure 6F:
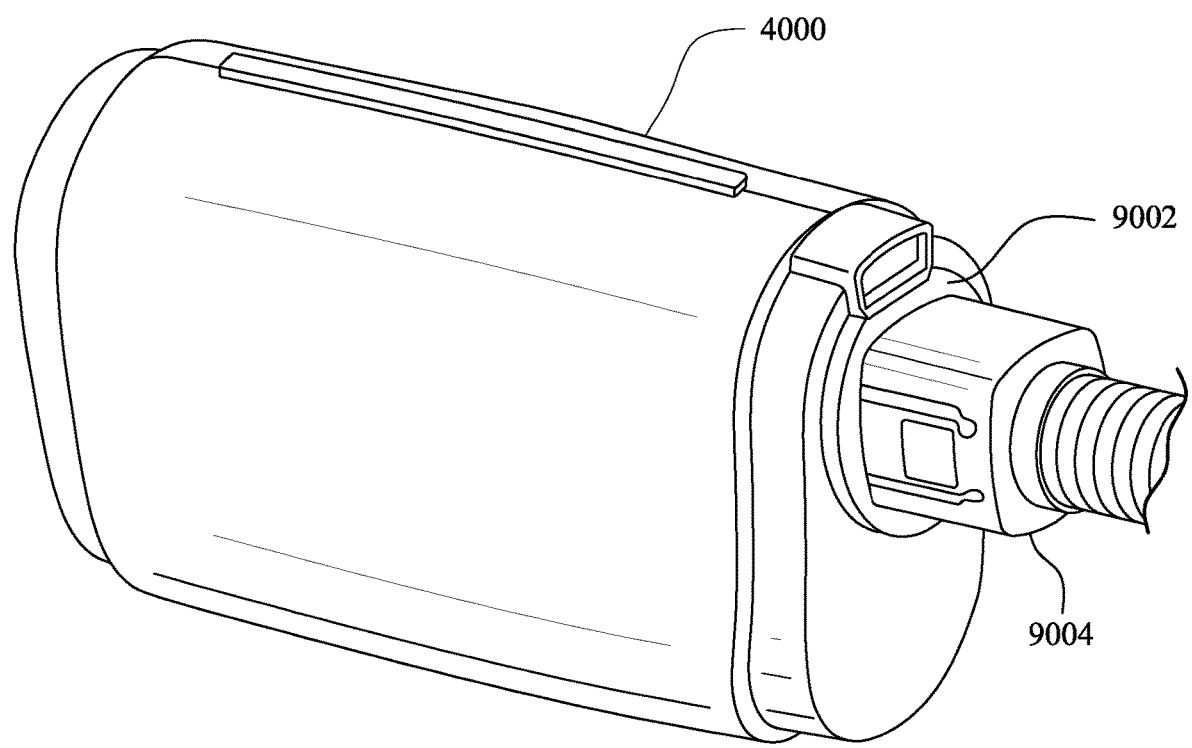

FIG. 6F shows a fluid connector with a first end and a second end connected together and the first end integrated into an RPT device.

Figure 6G:
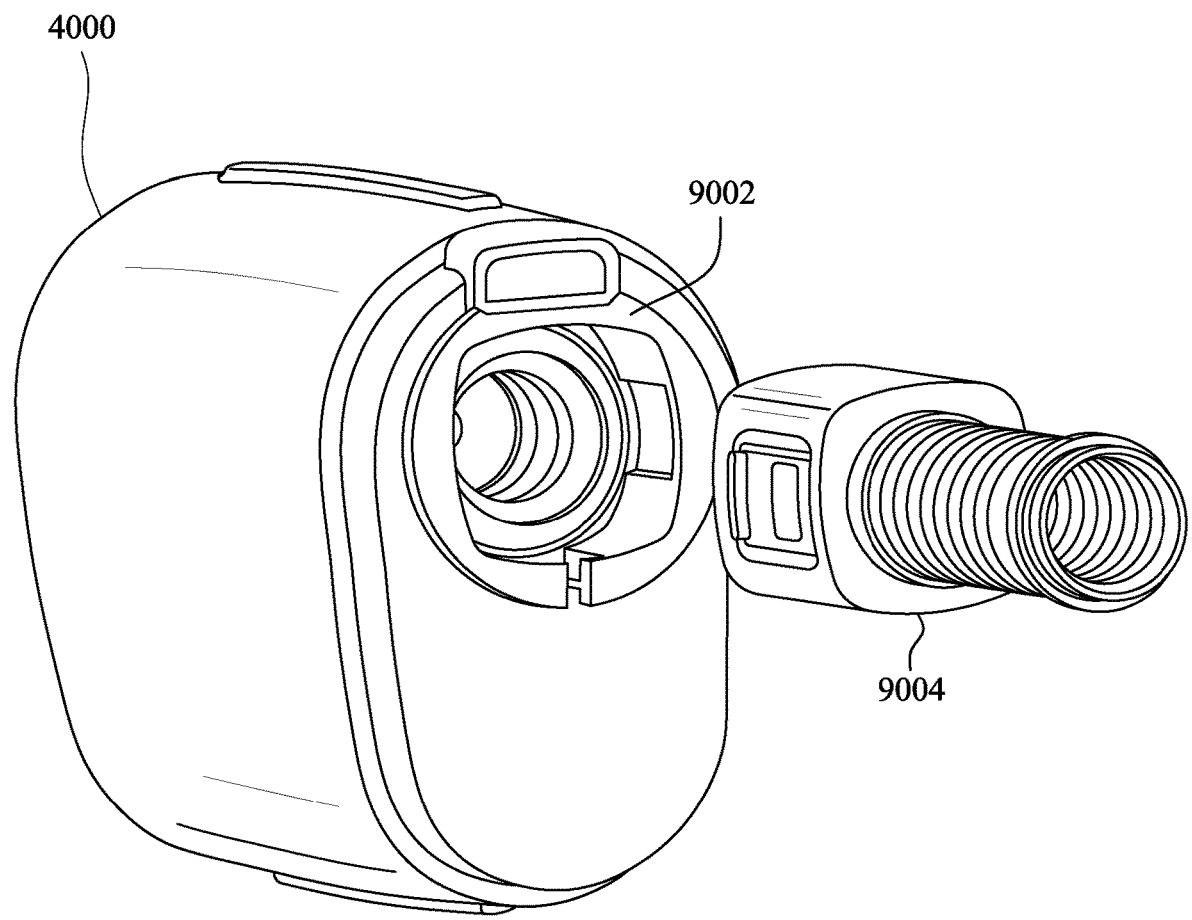
Figure 6H:
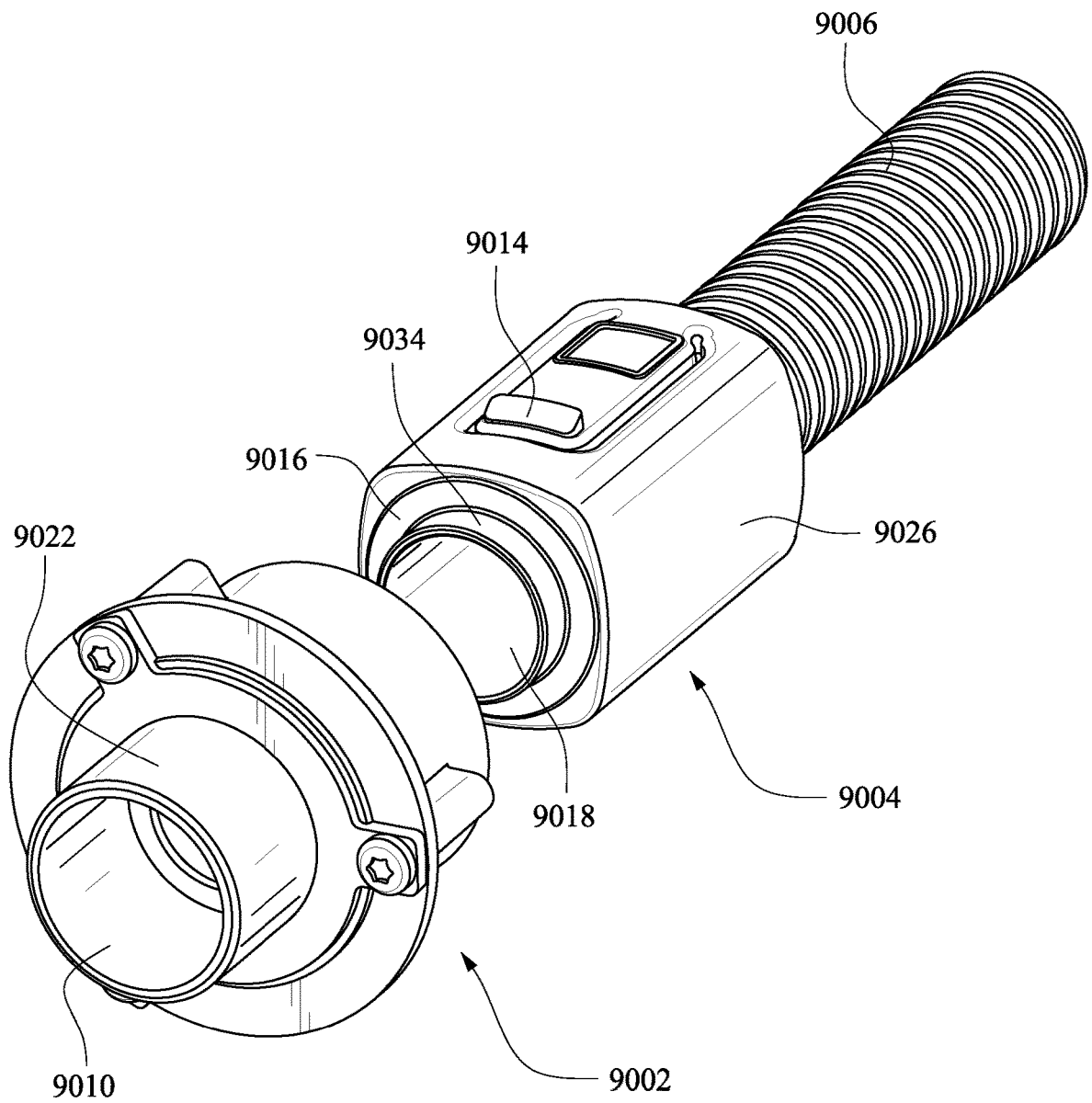

FIG. 6G shows a fluid connector with a first end and a second end disconnected and the first end integrated into an RPT device FIG. 6H shows a perspective view of a fluid connector with a first end and a second end separated from one another with the sealing surface of the second end being visible.

Figure 7A:
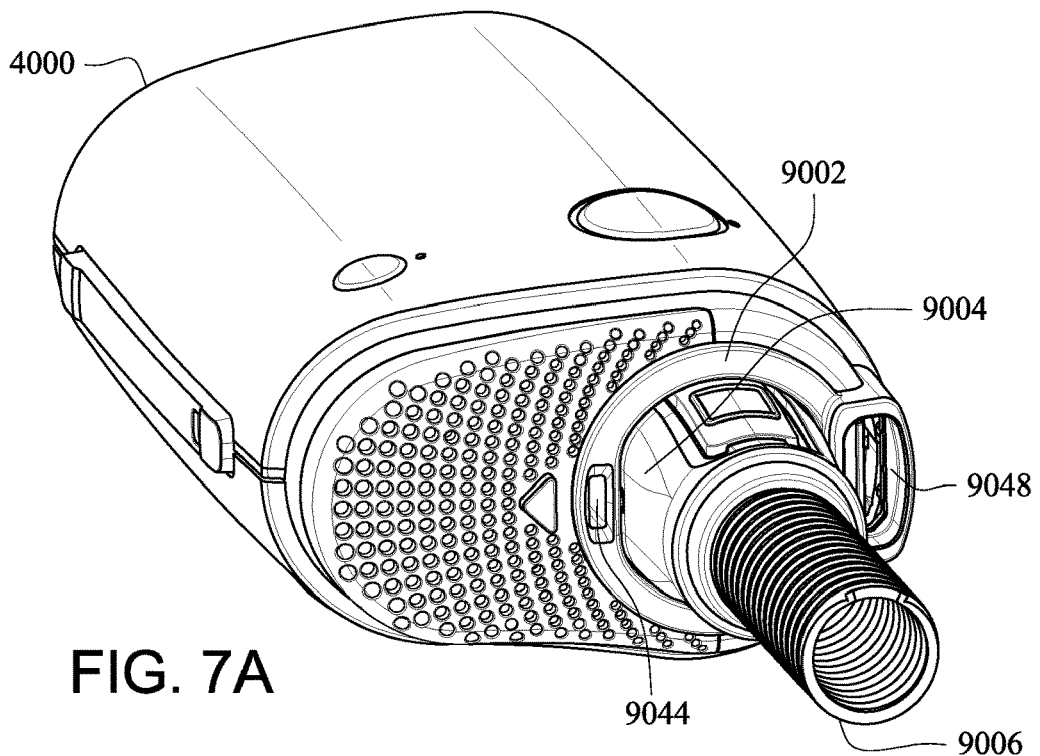

FIG. 7A shows a perspective view of a fluid connector incorporated with an RPT device according to another example of the present technology.

Figure 7B:
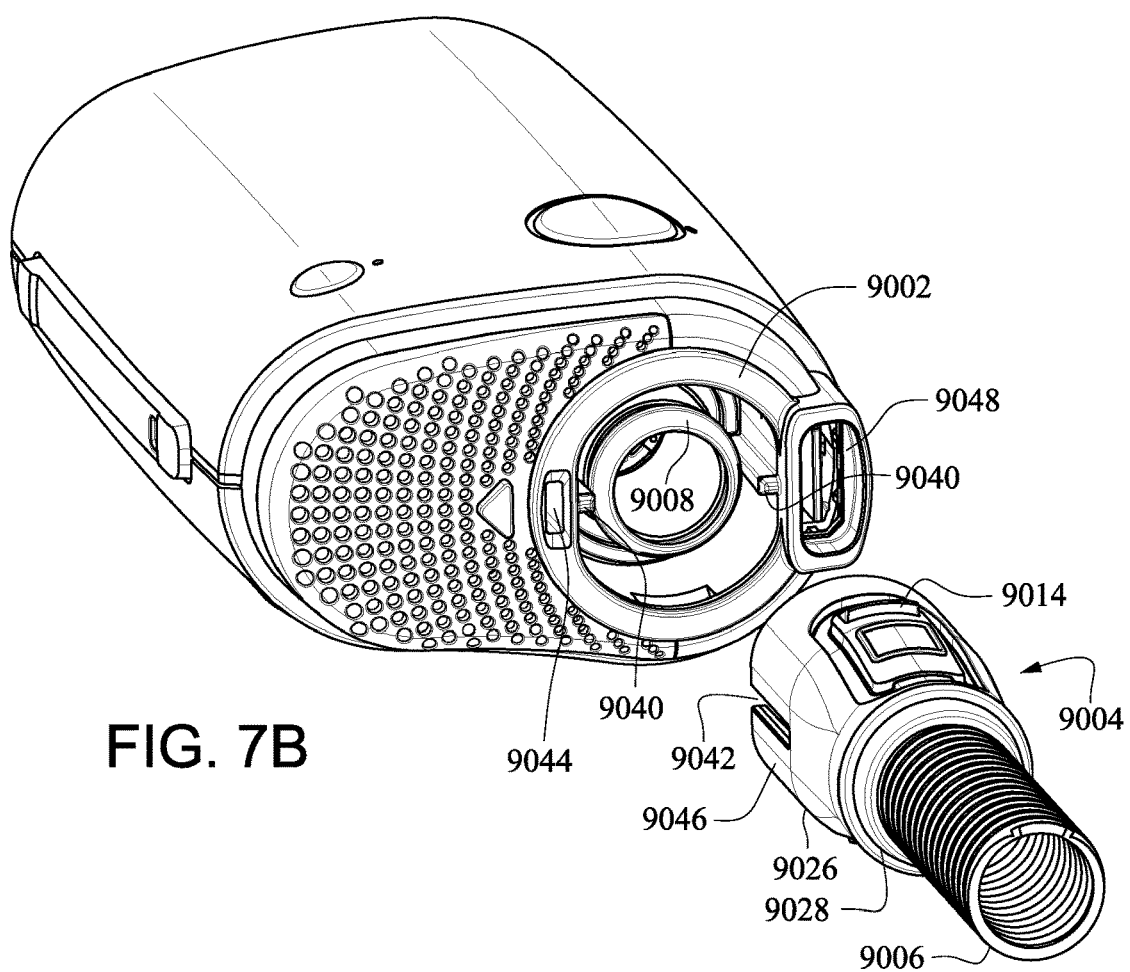

FIG. 7B shows a perspective view of the fluid connector and RPT device of FIG. 7A with the connector disconnected.

Figure 7C:
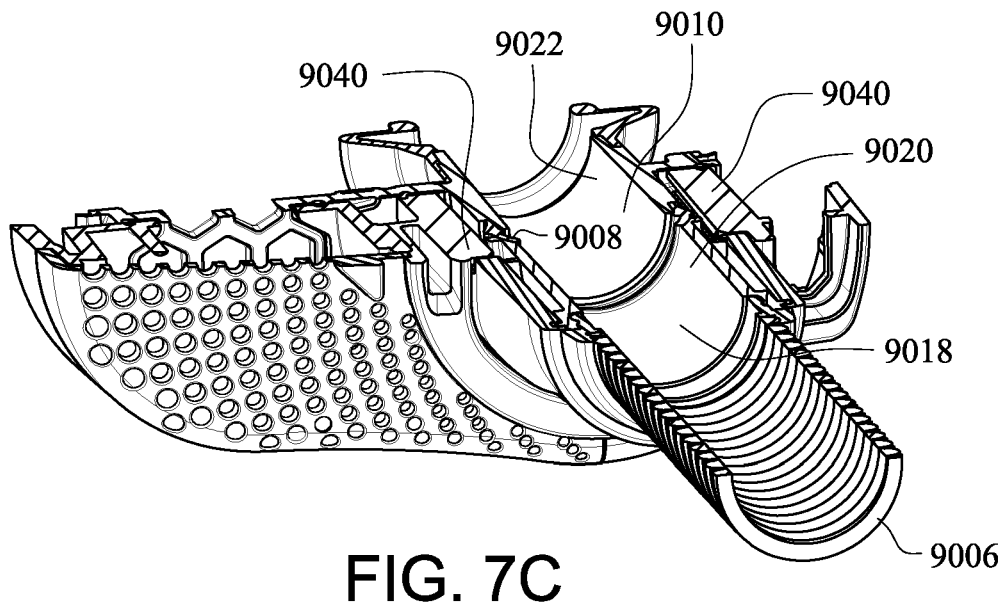

FIG. 7C shows a cross-section taken through FIG. 7A with most of the RPT device omitted.

Figure 7D:
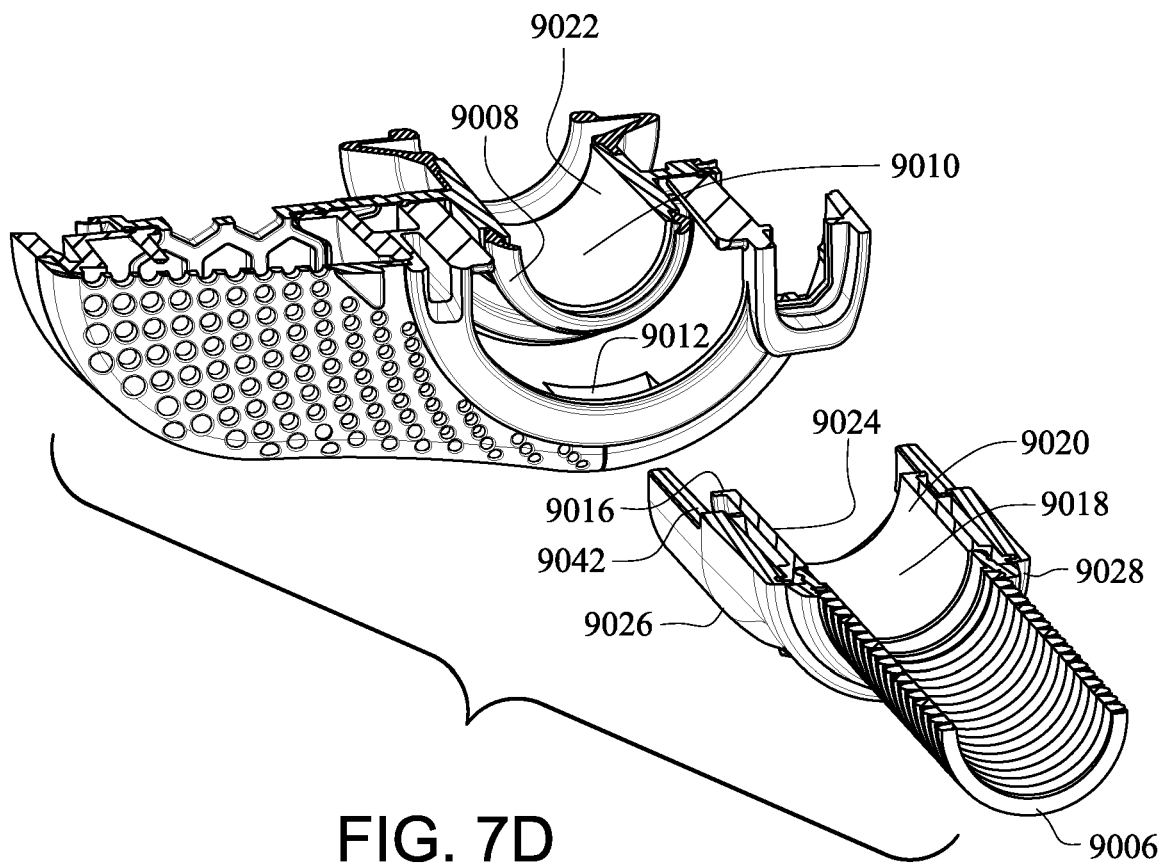

FIG. 7D shows a cross-section taken through FIG. 7B with most of the RPT device omitted.

Figure 7E:
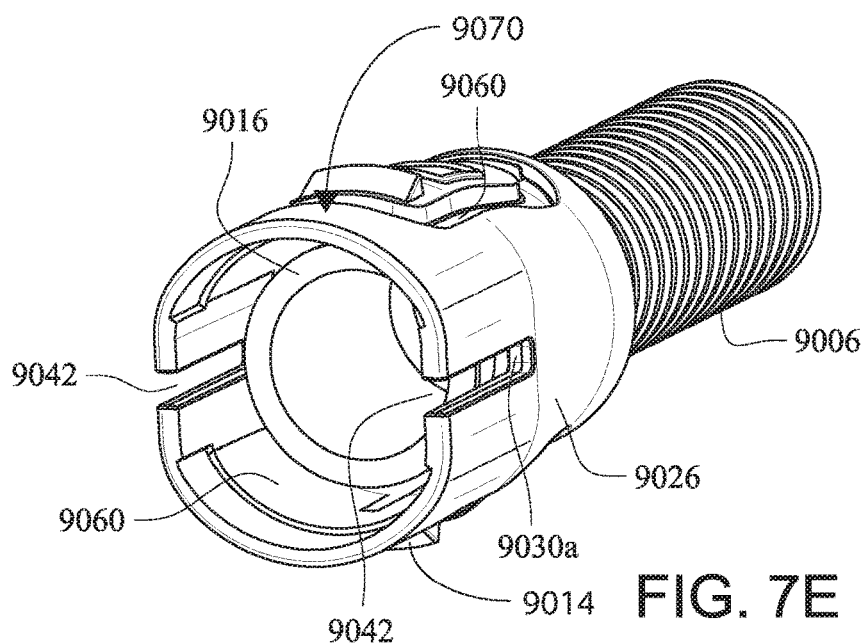

FIG. 7E shows a perspective view of half of the fluid connector of FIG. 7A.

Figure 7F:
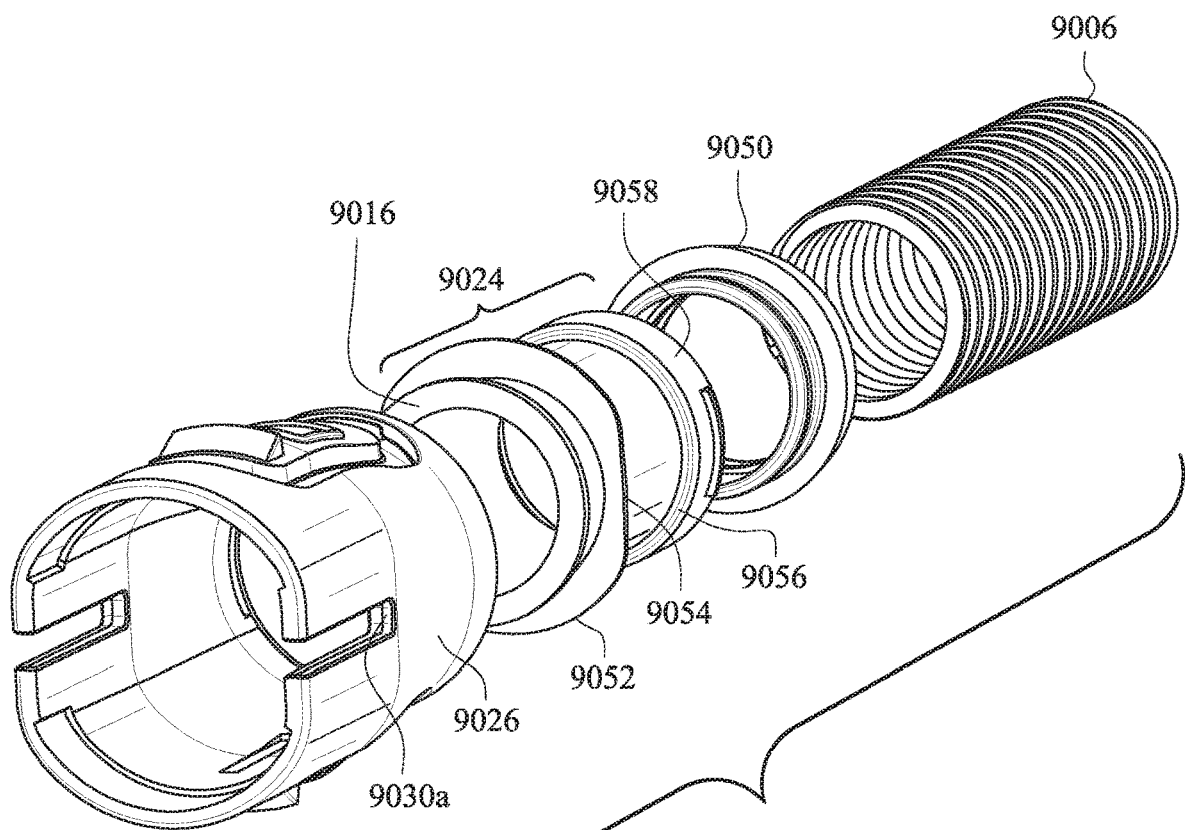

FIG. 7F shows an exploded view of the half of the fluid connector of FIG. 7E.

Figure 7G:
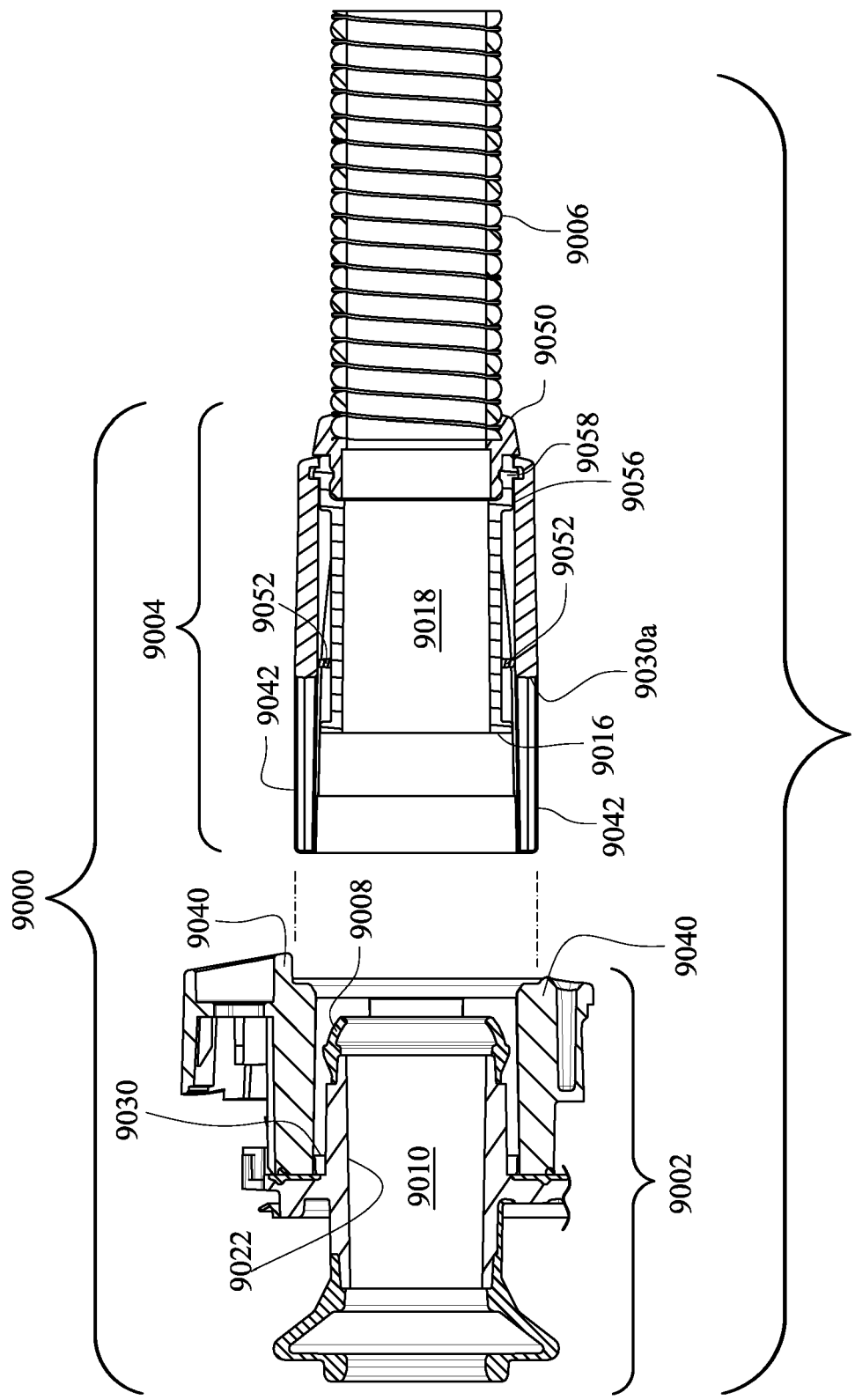

FIG. 7G shows a cross-section of a disconnected fluid connector according to an example of the present technology.

Figure 7H:
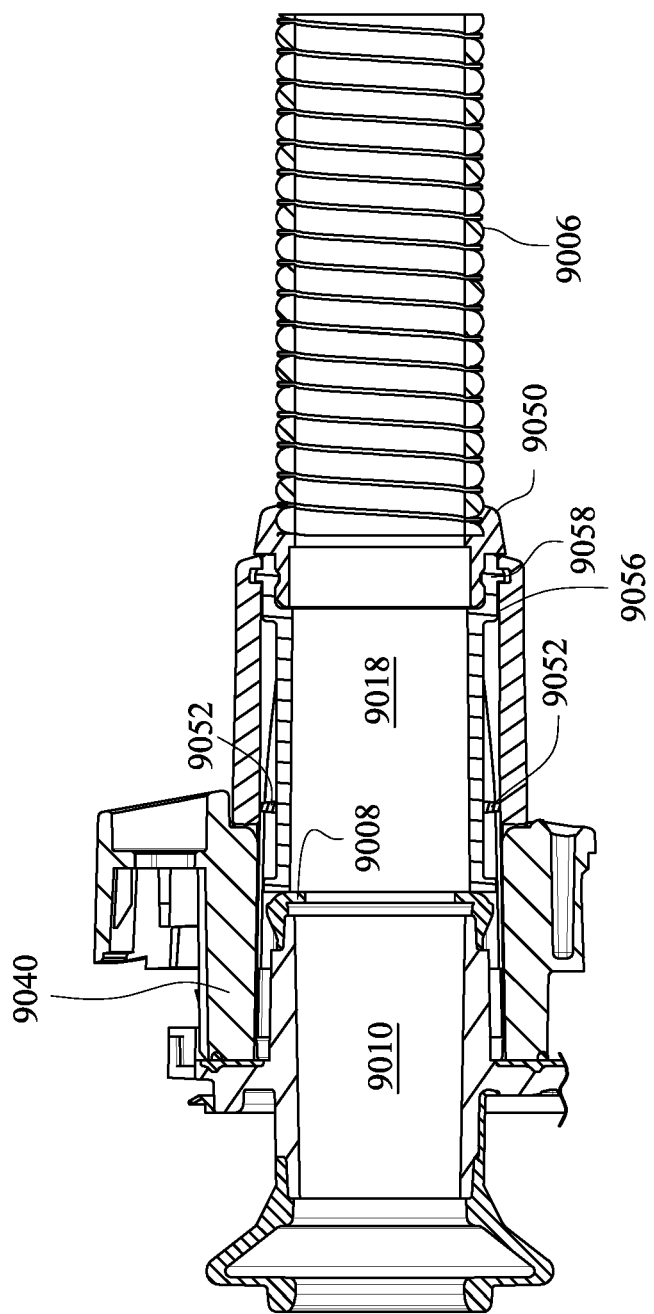
Figure 71:
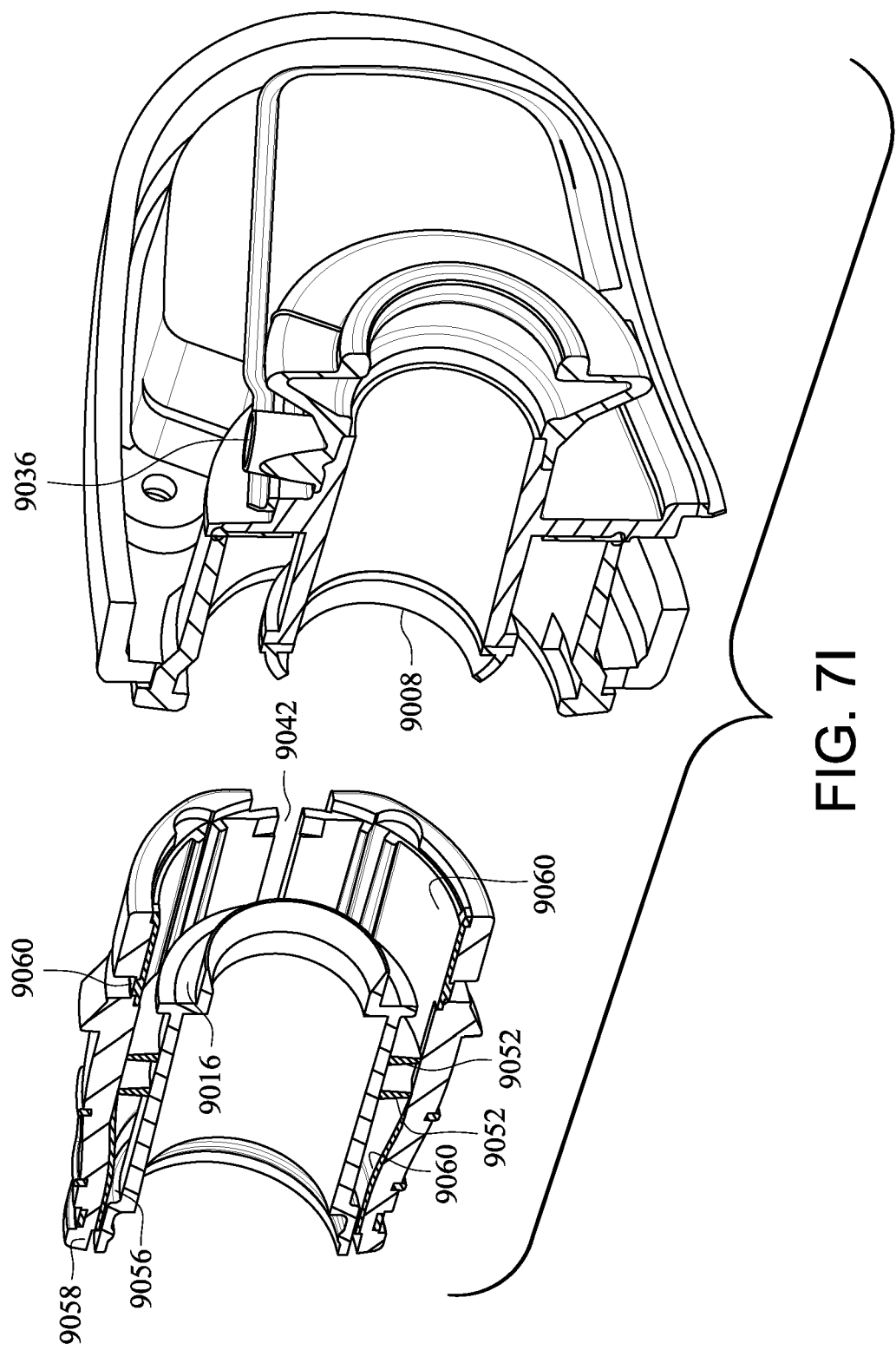

FIG. 7H shows a cross-section of the fluid connector of FIG. 7G that is connected.

FIG. 7I shows a perspective, cross-section of a fluid connector according to another example of the present technology.

Figure 7J:
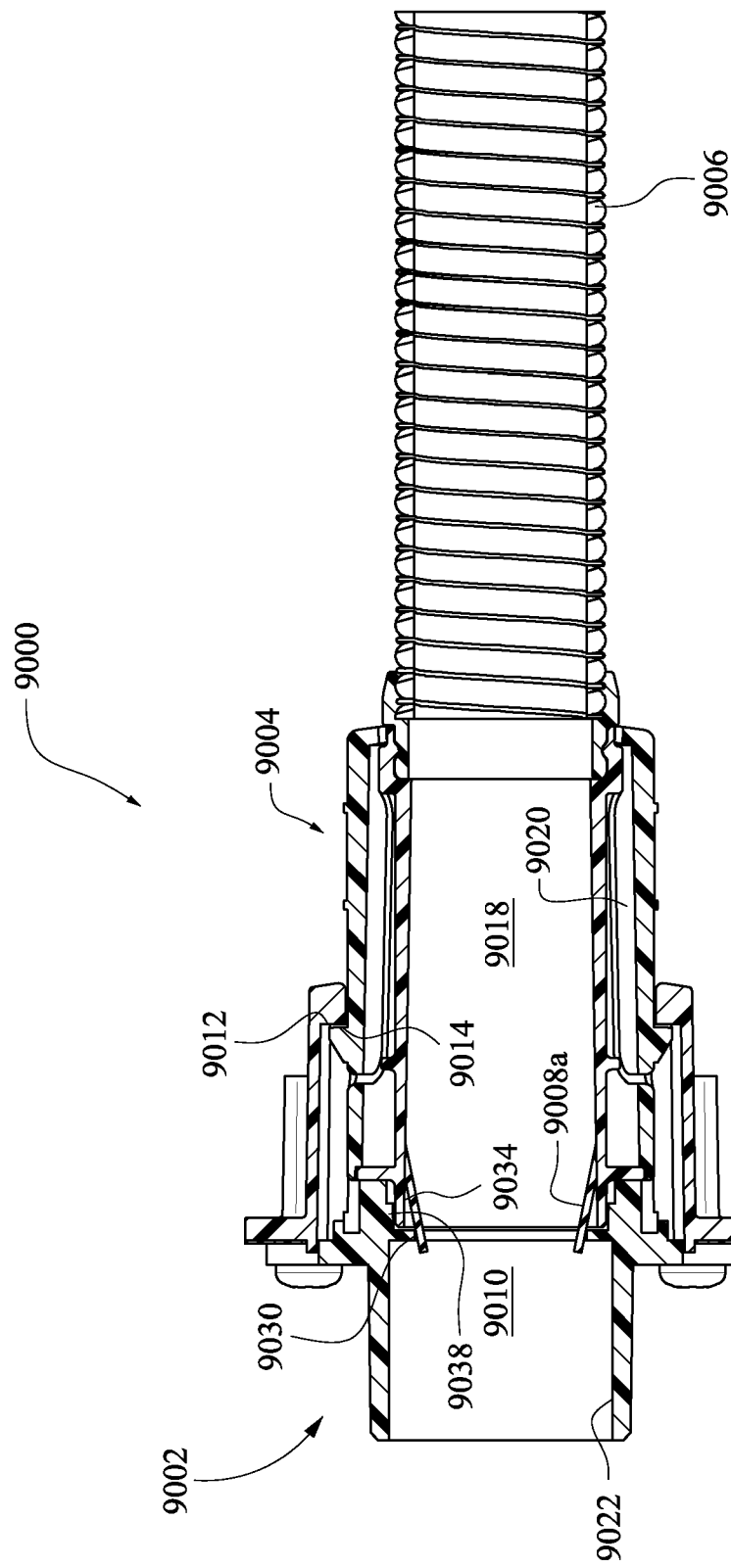

FIG. 7J shows a cross-section of a fluid connector according to another example of the present technology.

Figure 7K:
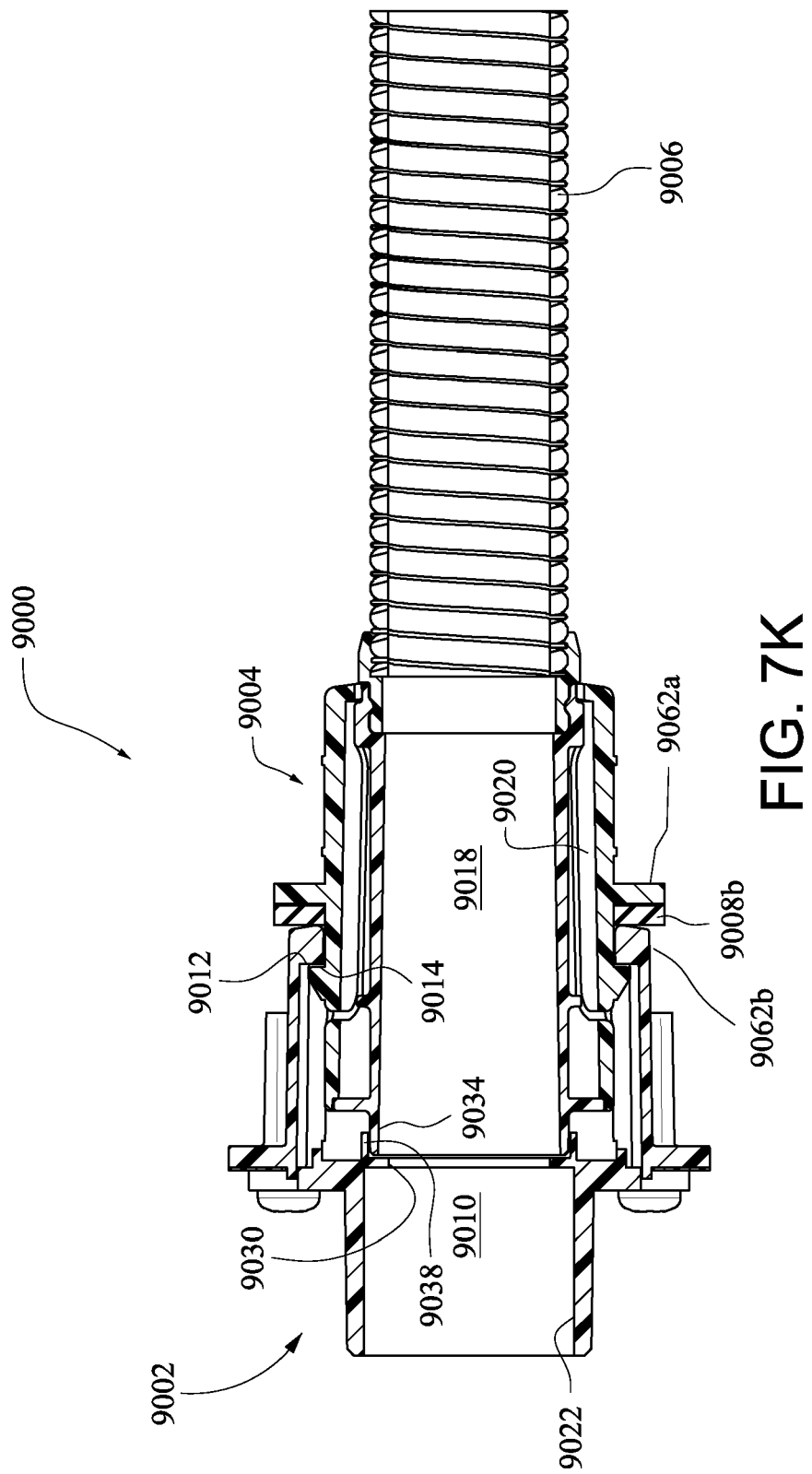

FIG. 7K shows a cross-section of a fluid connector according to another example of the present technology.

Figure 7L:
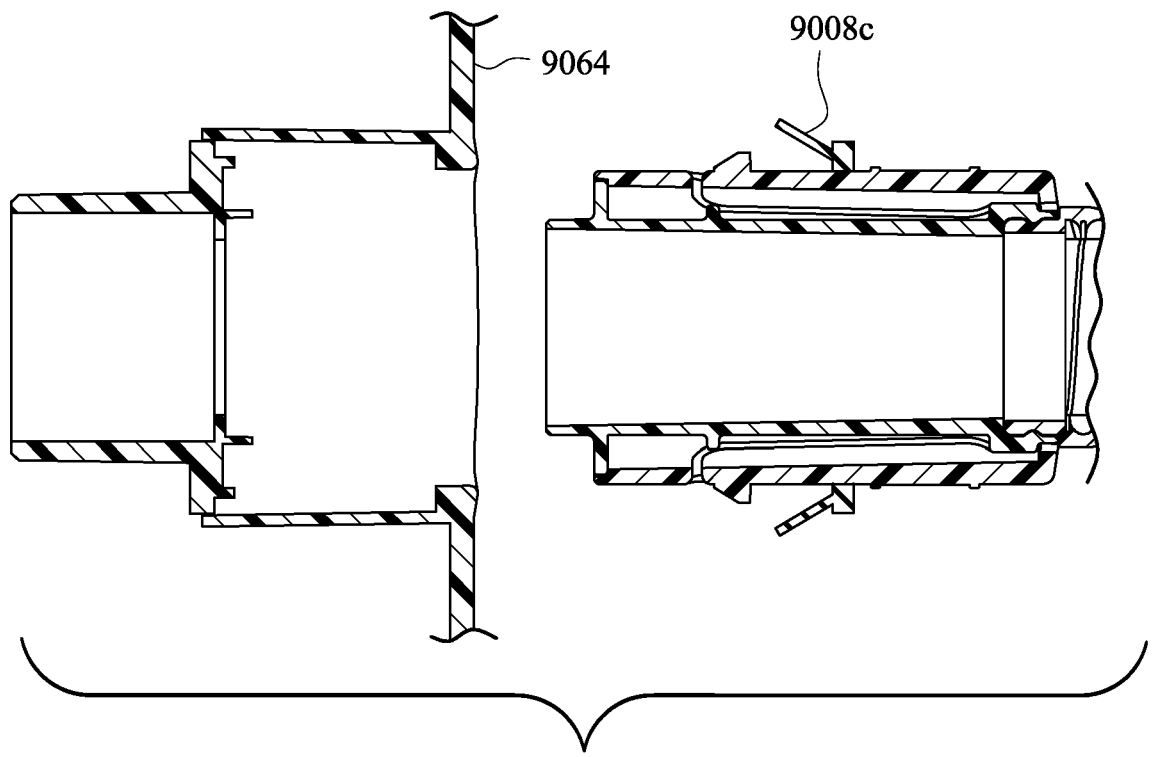

FIG. 7L shows a cross-section of a fluid connector according to another example of the present technology.

Figure 7M:
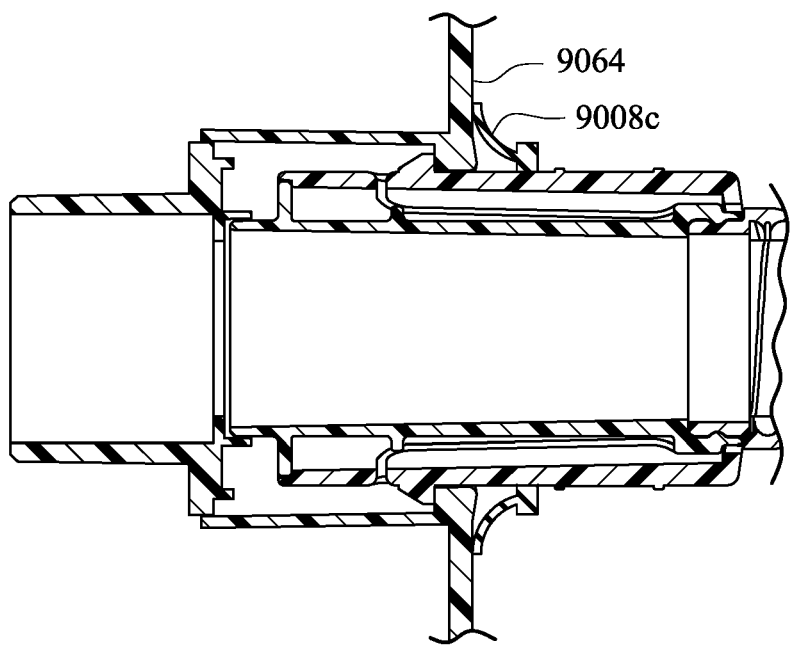

FIG. 7M shows a cross-section of a fluid connector according to another example of the present technology.

Figure 7N:
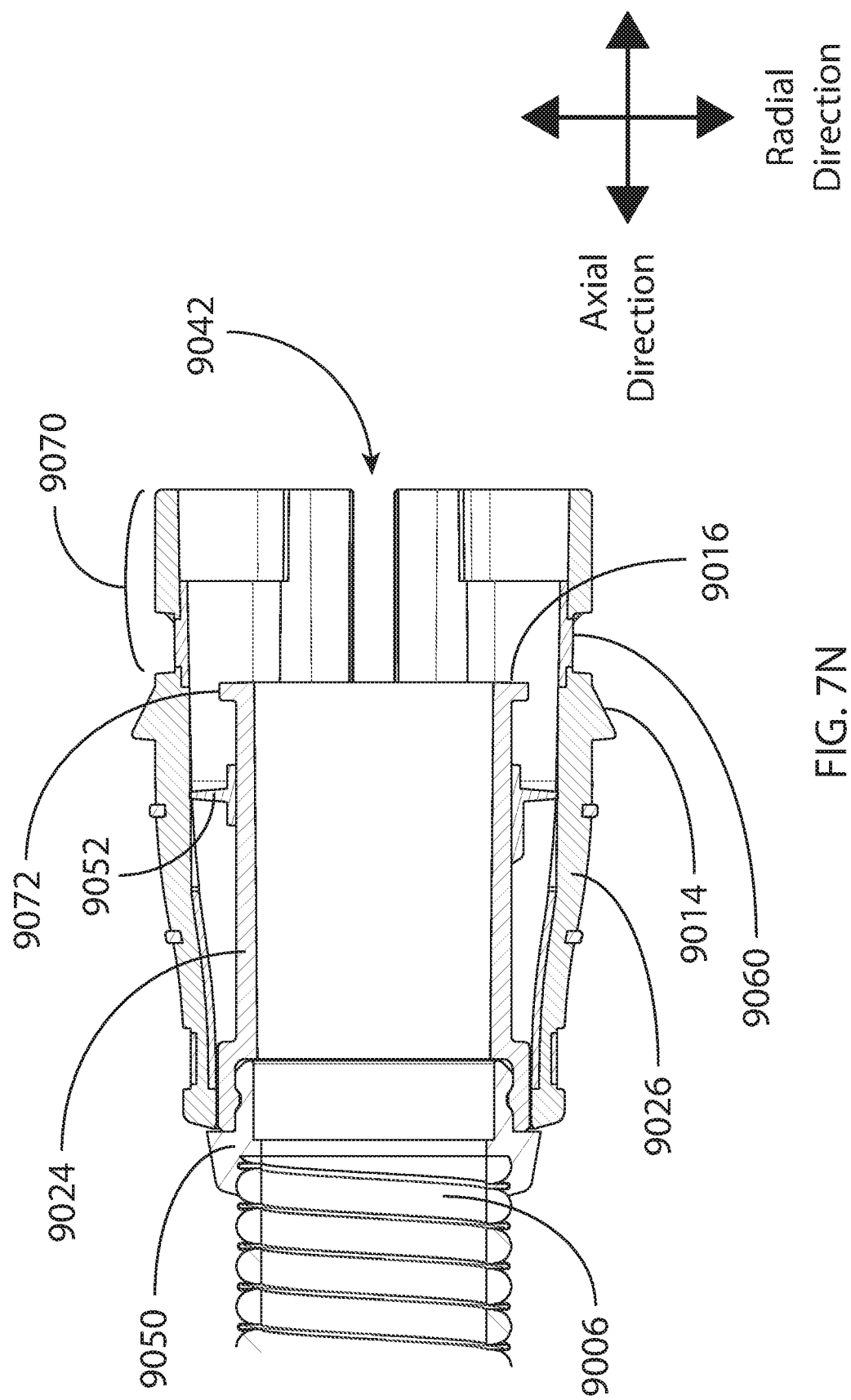

FIG. 7N shows a cross-section of an end of a fluid connector according to another example of the present technology.

Figure 8A:
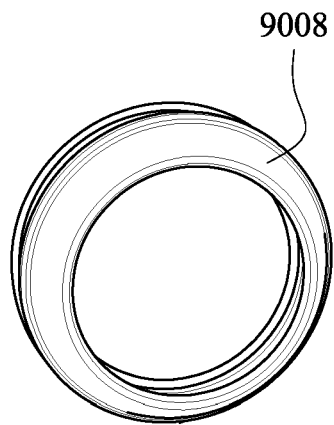

FIG. 8A shows a seal for a fluid connector according to the present technology.

Figure 8B:
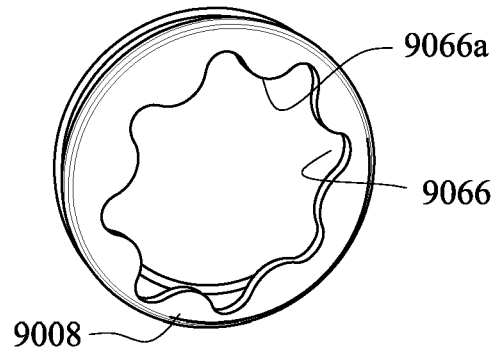

FIG. 8B shows a seal for a fluid connector according to the present technology.

Figure 9:
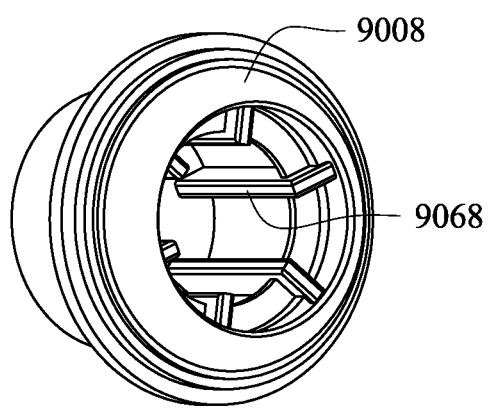

FIG. 9 shows a seal for a fluid connection and adjacent structure according to the present technology.

4 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting. For example, terms such as first, second and third are included to differentiate similarly described features but a feature indicated as a second feature in the description may be recited in a claim as a first feature.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

4.1 THERAPY

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

4.2 TREATMENT SYSTEMS

Figure 1A:
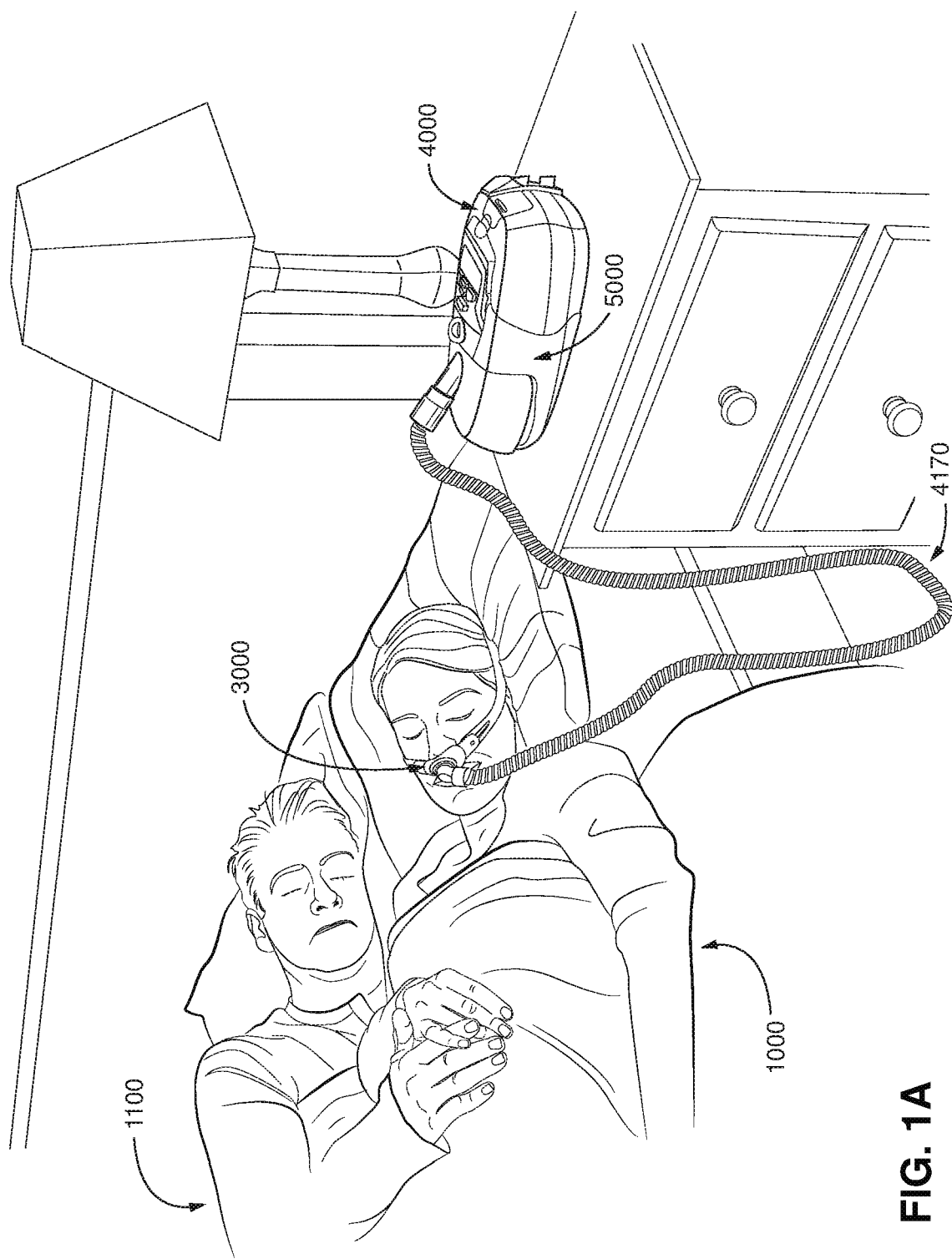
Figure 2A:
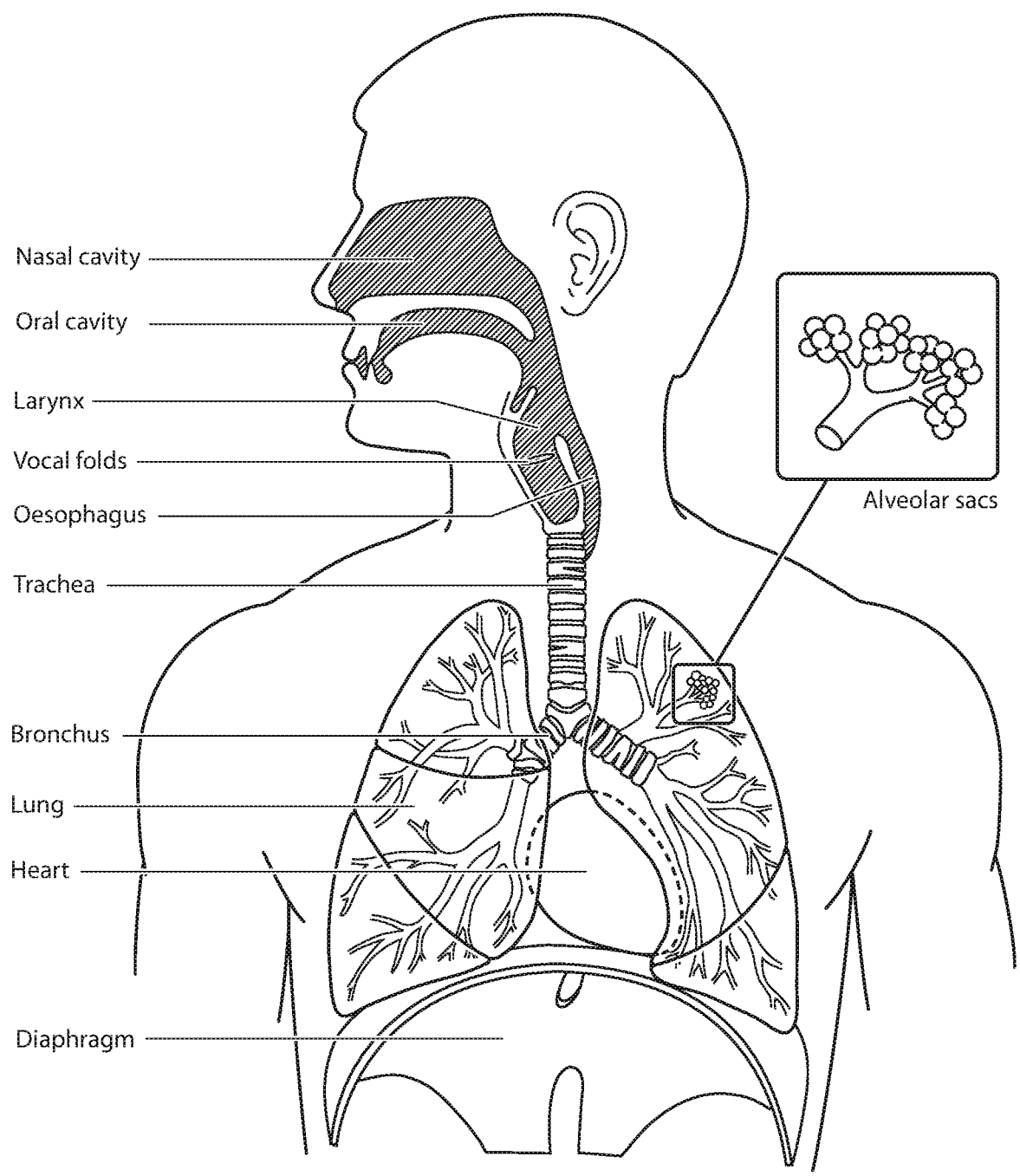

In one form, the present technology comprises an apparatus or device for treating a respiratory disorder. The apparatus or device may comprise an RPT device 4000 for supplying pressurised air to the patient 1000 via an air circuit 4170 to a patient interface 3000, for example as shown in FIG. 1A.

4.3 PATIENT INTERFACE

Figure 3A:
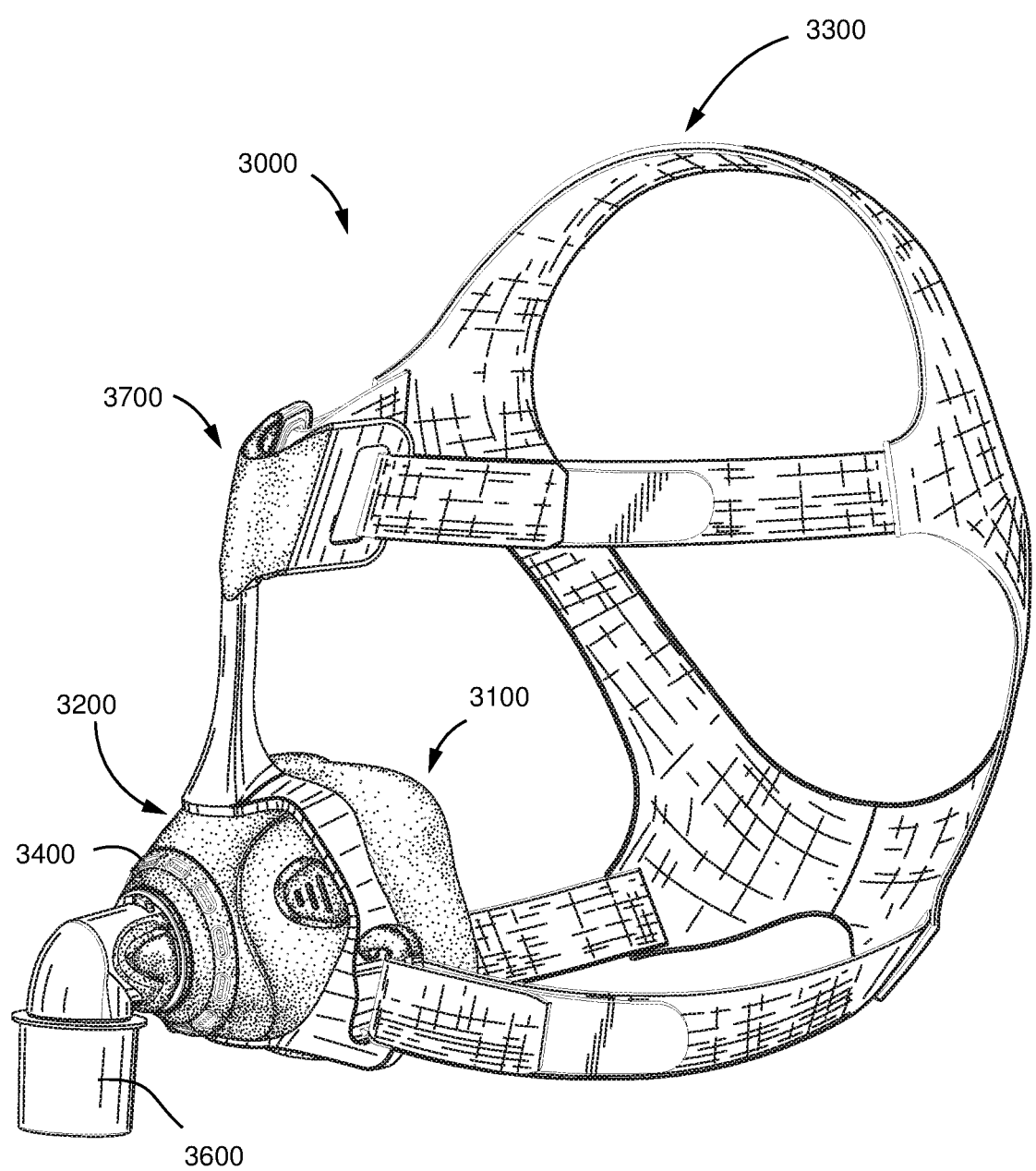
Figure 4A:
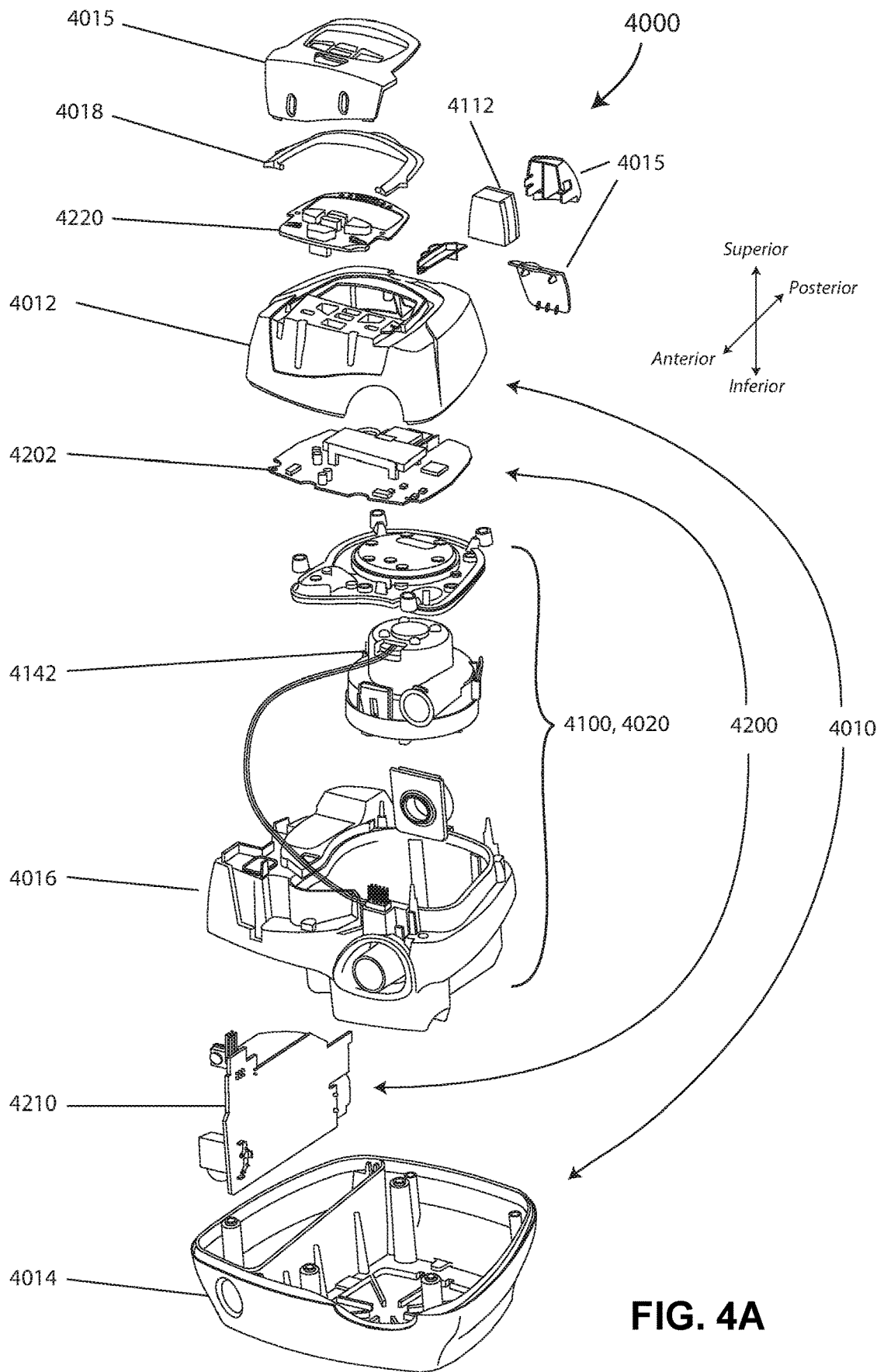
FIG. 4A shows an RPT device in accordance with one form of the present technology.
Figure 4B:
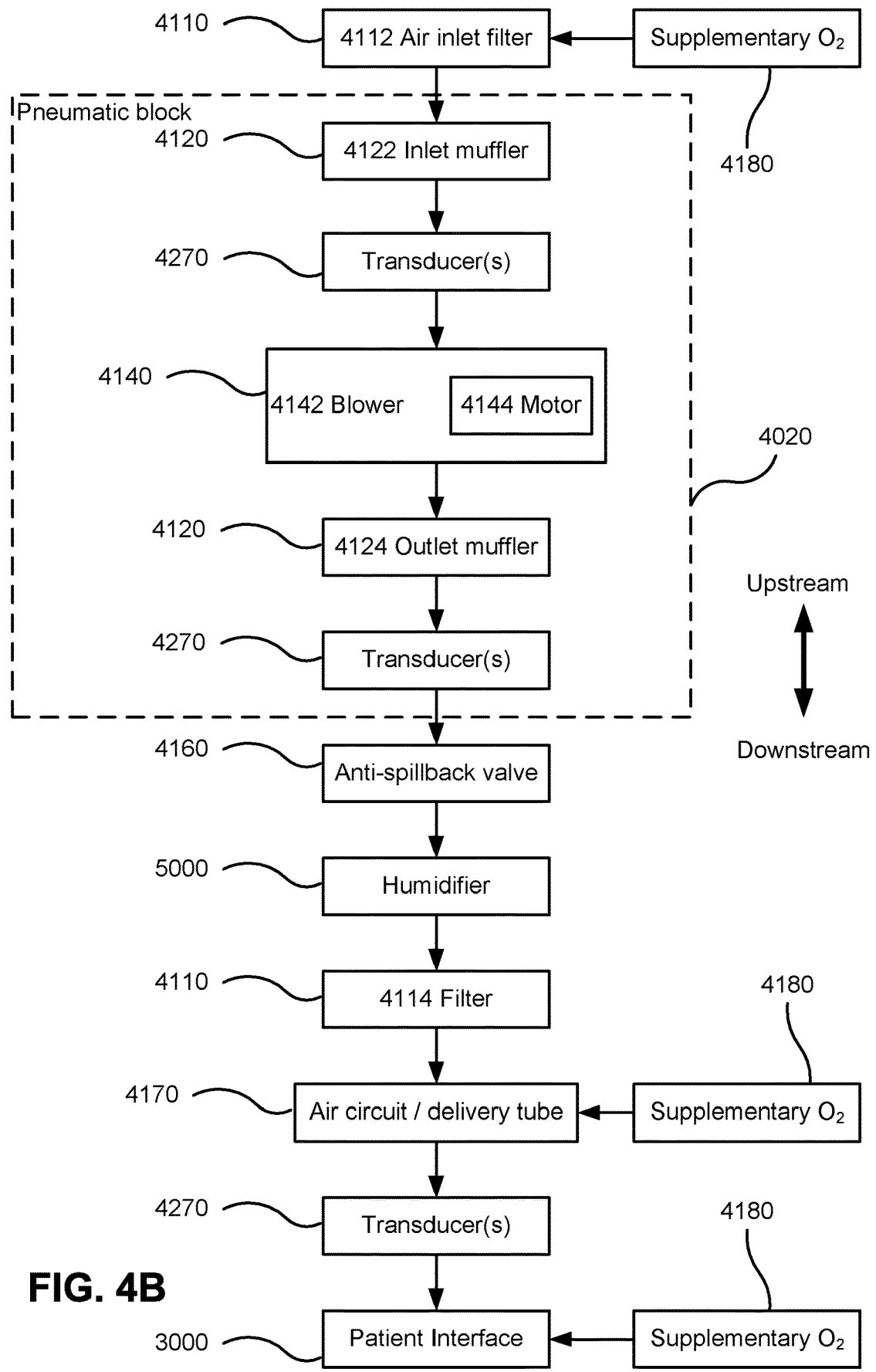
FIG. 4B is a schematic diagram of the pneumatic path of an RPT device in accordance with one form of the present technology. The directions of upstream and downstream are indicated.

A non-invasive patient interface 3000 (e.g. see FIG. 3A) in accordance with one aspect of the present technology comprises the following functional aspects: a seal-forming structure 3100, a plenum chamber 3200, a positioning and stabilising structure 3300 and one form of connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

4.3.1 Vent

In one form, the patient interface 3000 includes a vent 3400 constructed and arranged to allow for the washout of exhaled carbon dioxide.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure 3500, e.g., a swivel 3510.

In some forms, one or more vents may be located elsewhere in a treatment system, such as discrete from the patient interface 3000.

4.4 RPT DEVICE

An RPT device 4000 in accordance with one aspect of the present technology comprises mechanical and pneumatic components 4100, electrical components 4200 and is configured to execute one or more algorithms 4300. The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

Another suitable example of an RPT device is described in U.S. Provisional Patent Application 62/189,483, the entire contents of which is incorporated herewithin by reference.

4.4.1 RPT Device Mechanical & Pneumatic Components

An RPT device may comprise one or more of the following components in an integral unit. In an alternative form, one or more of the following components may be located as respective separate units.

4.4.1.1 Pressure Generator 4140

In one form of the present technology, a pressure generator 4140 for producing a flow, or a supply, of air at positive pressure is a controllable blower 4142. For example the blower 4142 may include a brushless DC motor 4144 with one or more impellers housed in a volute. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

4.4.1.2 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

4.4.1.3 Air Circuit

An air circuit 4170 in accordance with an aspect of the present technology is a conduit or a tube constructed and arranged in use to allow a flow of air to travel between two components such as the pneumatic block 4020 and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230 or a humidifier controller 5250. One example of an air circuit 4170 comprising a heated wire circuit is described in United States Patent Application No. US/2011/0023874, which is incorporated herewithin in its entirety by reference.

4.5 HUMIDIFIER

4.5.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

4.6 FLUID CONNECTOR

FIG. 6A illustrates a side view of a fluid connector 9000 with a first end 9002 and a second end 9004 mated with one another. A portion of a fluid conduit 9006, which may be part of the air circuit 4170, is connected to the second end 9004. Instead of the fluid conduit 9006, an adaptor or connector to a fluid conduit may be provided. An outlet of an RPT device 4000 may comprise a second end 9004 in some forms of the present technology.

The fluid connector 9000 may be configured to removably form a sealed connection to allow a flow of air to travel therethrough, such as from the RPT device 4000 to the patient interface 3000. The fluid connector 9000 may comprise a plurality of components, such as a first end 9002 and a second end 9004, which may be releasably connected to each other to make and/or break the sealed connection.

The first end 9002 and the second end 9004 may form a pneumatic path therebetween via complementary sealing portions, and be retained to each other by complementary retaining portions that may be separate portions to the complementary sealing portions. Accordingly, each of the first end 9002 and the second end 9004 may comprise a separate sealing portion and a retaining portion, as is described in further detail elsewhere in the present document.

Where the sealing function and the retaining function are performed by separate complementary portions, each of the sealing and/or the retaining functions may be more readily optimised, to address one or more of competing design requirements. For example, where one pair of complementary portions function to seal and retain two components, formation of a tight seal may lead to a high frictional force, decreasing ease of connection and/or disconnection of the components.

Furthermore, where the usability of connection/disconnection is improved, the seal may not be as robust, such as in cases where the two components may be subject to forces and/or torques in varying directions and magnitudes. In the cases of a fluid connector such as those described in the present document, a patient wearing a patient interface 3000 may move about while asleep, or preparing to go to sleep, causing the fluid connector to be pulled and/or twisted in various directions.

Thus, one aspect of the present technology relates to a fluid connector 9000, wherein the first end 9002 and the second end 9004 are connected, or connectable, to each other by complementary sealing portions and complementary retaining portions.

In one form, the first end 9002 and the second end 9004 may comprise complementary sealing portions to form an air seal when connected. The air seal may be configured to form and maintain a sealing engagement to allow a flow of air to travel therethrough. The sealing engagement may be sufficient to allow a pressurised flow of air to travel therethrough, such as at pressures between 4 cm $H_2O$ to 40 cm $H_2O$ to provide respiratory therapies.

In some forms, the first end 9002 and the second end 9004 may comprise complementary portions to retain the first end 9002 and the second end 9004. The retaining portions may maintain the first end 9002 and the second end 9004 in sealing engagement with each other, such as by preventing accidental disengagement. The retaining portions may comprise latching mechanisms as will be detailed further in the present document.

FIG. 6B illustrates a sectional view of the fluid connector 9000 where the first end 9002 and the second end 9004 are not connected to one another. In this view, a seal portion 9008 is visible. The seal portion 9008 may be formed from any material that is suitable for forming a seal in an air path of a device that provides breathing gas to a patient, for example, silicone or thermoplastic elastomer (TPE). The seal portion 9008 extends around a first opening 9010, which is illustrated as the interior of a first tube 9022. A latching portion 9012, which may be in the form of a recess, is provided in the first end 9002. The latching portion 9012 may be provided on opposed sides as illustrated in FIG. 6*b*, on a single side or all around a periphery of the first end 9002. As illustrated, the latching portion 9012 is an undercut that is substantially perpendicular to a central axis of the first end 9002. Other angles are possible depending on the retention force desired.

The second end 9004 includes a sealing surface 9016. The sealing surface 9016 may be formed circumferentially around a second opening 9018 that is illustrated as the interior of a second tube 9020. The sealing surface 9016 is illustrated as a substantially annular surface that extends radially and perpendicularly (i.e., at 90°) away from the second tube 9020. This may result in the sealing surface 9016 being substantially perpendicular to a direction of the fluid flow from the first end 9002 to the second end 9004. However, the sealing surface 9016 could also extend outward at an angle such that the sealing surface 9016 is beveled. For example, the sealing surface could be at 85°, 80°, 75°, 70°, 65°, 60°, 55°, 50° or 45° angle, positive or negative, or any value in between. As can be seen in FIG. 6B, the second tube 9020 may comprise an overhang portion 9034 that extends beyond the sealing surface 9016 towards the seal portion 9008. This may result in the overhang portion 9034 of the second tube 9020 extending through the seal portion 9008 as illustrated in FIG. 6C. It will be understood that the second tube 9020 need not comprise an overhang portion in some examples of the present technology.

The overhang portion may be configured to align the first end 9002 with the second end 9004 in one or more directions. The overhang portion 9034 may be configured to be inserted into a guide portion 9038 on the first end 9002 to act as a lead-in and align the second end 9004 with the first end 9002 in a radial (or transverse) direction. Thus the first end 9002 and second end 9004 may have a male/female relationship. Additionally, a stop 9030 may be provided to limit travel of the second tube 9020, for example by abutting the overhang portion 9034 at the limit of travel. Although the overhang portion 9034 is shown as a tube, the overhang portion may not extend continuously around a circumference of the second end 9004, as it would be internal to the seal created by the complementary sealing portions (seal portion 9008 and sealing surface 9016). The overhang portion may extend only partially through the seal portion 9008, such as in castellated extensions, tabs, ribs and the like.

With the configuration illustrated in FIG. 6C, the interior flow path of the fluid connector 9000 defined by the first tube 9022, second tube 9020 and stop 9030 may have very little flow restriction because the interior flow path is substantially the same as the interior of the fluid conduit 9006, for example as evaluated in cross section shape and size. Thus the fluid connector 9000 may have negligible pressure drop when air is flowing through the fluid connector 9000 throughout a patient's breathing cycle and therapy pressure (e.g., at pressures between 4 cm $H_2O$ to 40 cm $H_2O$).

The seal portion 9008 may include a portion that contacts the sealing surface 9016 in any form that is suitable for forming a face seal, such as by tangential contact therebetween. As illustrated, the seal portion 9008 contacts the sealing surface 9016 with a substantially frustoconical shape, which is similar to a bellows-shape or partial bellows-shape. Alternatively, a partial spherical, or partial toroidal surface may be provided on the seal portion 9008. With any of these shapes, the seal portion 9008 may contact the sealing surface 9016 before the latching portion 9012 and complementary latching portion 9014 are fully or even partially engaged. Alternatively, the seal portion 9008 and sealing surface 9016 may be separated by a gap even after the latching portion 9012 and complementary latching portion 9014 are fully engaged. In this scenario, internal pressurization may cause the seal portion 9008 to move into contact with the sealing surface 9016 and form a seal.

The seal portion 9008 may comprise a resilient and compliant material such that it may deform under load, while maintaining its original configuration when the load is removed therefrom. The seal portion 9008 may be configured to be readily deformed under load to form and/or maintain a seal with the sealing surface 9016. In some forms, the seal portion 9008 may comprise a membrane composed of silicone. The silicone membrane seal portion 9008 may be sufficiently compliant that it would deform to move into contact with the sealing surface 9016 due to the pressure caused by the air flow. The silicone membrane seal portion 9008 may additionally or alternatively be sufficiently compliant such that it would maintain a sealing engagement with the sealing surface 9016 even when compressed from its undeformed configuration.

The proposed configurations of the seal portion 9008 may provide a seal that is compliant with respect to a mating direction between the first end 9002 and the second end 9004 (e.g., leftwards in FIG. 6*b*) and/or compliant in a direction radial to an axis defined by a direction of engagement between the first end 9002 and the second end 9004 (e.g., up and down in FIG. 6*b*).

The force necessary to compress the seal portion 9008 (e.g. when compression is required to form and/or maintain a seal) may be sufficiently low so as to not be a significant compressive force. For example, the force required to compress the seal portion 9008 may be less than a force required to engage the latching portion 9012 with the complementary latching portion 9014, such as to overcome any friction in connecting the second end 9004 and the first end 9002. Alternatively, the force required to compress the seal portion 9008 may be less than half of the force required to engage the latching portion 9012 with the complementary latching portion 9014. Alternatively, the force required to compress the seal portion 9008 may be less than one tenth of the force required to engage the latching portion 9012 with the complementary latching portion 9014. Thus in a configuration where the seal portion 9008 contacts the sealing surface 9016 before the latching portion 9012 and complementary latching portion 9014 are fully engaged, a user may not encounter significant force that would be mistaken for full engagement. In some forms, any force caused by a compression of the seal portion 9008 for connection of the second end 9004 and the first end 9002 may be sufficiently small that it is substantially imperceptible to a user. That is, the force perceived by a user in a configuration wherein the seal portion 9008 is removed from the first end 9002 may be substantially identical to a configuration where the seal portion 9008 must be compressed for connection.

The shapes of the seal portion 9008 according to the present technology may provide a seal that is compliant opposite to a mating direction between the first end 9002 and the second end 9004 (e.g., rightwards in FIG. 6B). This may allow for a seal portion 9008 that can seal with the sealing surface 9016 even if a gap exists between seal portion 9008 and sealing surface 9016 when the fluid connector 9000 is unpressurized. When pressure is provided to an interior of the fluid connector 9000 (e.g., to the first tube 9022), the seal portion 9008 may expand towards and contact the sealing surface 9016 to form a seal. With this configuration, a user should not encounter any additional force when connecting the first end 9002 to the second end 9004 beyond the force necessary to engage the latching portion 9012 and complementary latching portion 9014.

Thus, the seal portion 9008 and the sealing surface 9016 may be configured to form a seal while remaining free from retention by each other. As a result, any latching or retaining function in the fluid connector 9000 may be separated from the sealing function.

Although specific configurations of the seal portion 9008 are discussed above, other configurations are possible. For example, some forms of the seal portion 9008 may include an o-ring or a gasket material.

Either the seal portion 9008 or the sealing surface 9016 or both may be configured such that misalignment between the seal portion 9008 and sealing surface 9016 still results in a seal between the seal portion 9008 and the sealing surface 9016. For example, the seal portion 9008 and/or the sealing surface 9016 may be configured to form a seal therebetween while allowing for a range of misalignments in radial (or transverse) and/or axial directions.

For example, the sealing surface 9016 may comprise an annular shape (as shown in FIG. 6H) configured to form a face seal with a surface of the seal portion 9008 in a plurality of radial positions. That is, the seal portion 9008 and the sealing surface 9016 may form a seal therebetween although an axis of the first tube 9022 and an axis of the second tube 9020 may be misaligned, for example by 0.5 mm, 1 mm, 1.5 mm, 2 mm, 3 mm or 4 mm. In one form, the sealing surface 9016 may comprise a sufficiently wide annular portion such that the seal portion 9008 may be able to form a seal thereto.

The second end 9004 also includes a complementary latching portion 9014. The complementary latching portion 9014 is illustrated as a cantilevered hook including an engagement protrusion that mates or engages with the latching portion 9012. As with the latching portion 9012, the complementary latching portion 9014 may be provided on a plurality of (e.g. opposed) sides as illustrated in FIG. 6B or on a single side. The complementary latching portion 9014 may be in the form of U-shaped or C-shaped cut-through as illustrated in FIG. 6D. The complementary latching portion 9014 may be depressed to engage or disengage the complementary latching portion 9014 from the latching portion 9012 and allow engagement or disengagement between the first end 9002 and the second end 9004. Although providing more than two of the complementary latching portion 9014 is possible, doing so may make it unnecessarily difficult to disengage the second end 9004 from the first end 9002.

The latching portion 9012 and the complementary latching portion 9014 may be configured to provide an audible or haptic feedback to the user when engaged or disengaged.

In combination, the stop 9030 and latching portion 9012 may define a predetermined distance (travel) that the second end 9004 can move with respect to the first end 9002 while the two ends are connected. For example, if a first axial distance between the stop 9030 and latching portion 9012 is greater than a second axial distance between an end of the second tube 9020 and the engagement protrusion on the complementary latching portion 9014, then the difference between the first axial distance and the second axial distance will define a predetermined amount of travel that is non-zero. If the first axial distance and the second axial distance are equal, then no travel will be possible. However, there may be benefits associated with a non-zero travel at least with respect to ease of manufacture because a non-zero travel will allow for manufacturing tolerance that may reduce cost. Thus it may also be beneficial for the seal portion 9008 to be configured to form a seal with the sealing surface 9016 with a worst case manufacturing tolerance and after a predetermined amount of wear and/or creep in the fluid connector 9000. The shapes for the seal portion 9008 discussed above may allow for the seal portion 9008 to account for such a worst case scenario.

As best seen in FIG. 6B, the second end 9004 may include an inner portion 9024 and an outer portion 9026 that are rotatably coupled to one another at an interface 9028. The inner portion 9024 may include the seal portion 9008 and the outer portion 9026 may include the complementary latching portion 9014. As illustrated, the inner portion 9024 is rigidly or fixedly connected to the fluid conduit 9006 such that the inner portion 9024 and the fluid conduit 9006 may rotate together with respect to the outer portion 9026. At least a part of the fluid conduit 9006 may be overmolded onto the inner portion 9024 to form the rigid connection therebetween. In other forms, the fluid conduit 9006 may be friction fit, or interference fit into the inner portion 9024 so as to form a rigid connection.

The inner portion 9024 and the outer portion 9026 may be configured such that one or more cavities, such as annular cavities, may be created when assembled. The cavities may assist the inner portion 9024 to rotate with respect to the outer portion 9026 by reducing the friction therebetween. Additionally, the cavities may reduce a weight of the connector, thereby providing an improved user experience. Furthermore, cavities may allow the latching portion 9014 to be depressed thereinto for engagement/disengagement, while maintaining a sealed air path through the connector.

As best viewed in FIG. 6D, the outer portion 9026 may have an outer profile that has four curved sides as well as smaller radii at corners, a combination of which may create a uniquely identifiable outer profile in comparison to a typical circular profile. The first end 9002 may include a complementarily shaped recess. Thus the first end 9002 includes a female portion and the second end 9004 includes a male portion. Including male and female portions in the above form, or any other non-standard shape or configuration, may provide benefits.

First, the fluid connector 9000 comprising non-standard shapes and/or configurations may not conform to industry standards (e.g., ISO 5356-1), which include use of a circular spigot including a lead-in taper, onto which a cuff (e.g. rubber) is inserted over. Although not confirming to an industry standard may seem counter intuitive, there may be benefits such as addressing shortcomings of the prior art connectors as described elsewhere in the present document.

For example, the fluid connector 9000 may be used to connect an RPT device and patient interface that are designed to operate optimally together. For example, the RPT device may provide a lower flow rate that can only be taken advantage of by a patient interface that is designed to operate with that lower flow rate (e.g. the patient interface may comprise a proprietary vent). Then, having a fluid connector 9000 that does not mate with an industry standard will ensure that only the correct RPT device and patient interface are used together. Second, particularly with the illustrated profile, the first end and the second end 9004 may be mated with one another only in a predetermined number of relative orientations (e.g., four). The present four-sided shape also may provide well-defined sides that are easy to identify and grip for actuation of the complementary latching portion 9014. Thirdly, a non-standard shape such as that described herein, or others, may allow a user to readily identify which end of a patient conduit 4170 may be a complementary connector to another connector, such as an outlet of the RPT device.

FIG. 6E illustrates another example of a present technology, wherein a port 9032 is included in the first end 9002. The port 9032 may be used to sense pressure downstream of a blower and outside of a housing of the blower, such as by sensing a pressure downstream of the RPT device. The port 9032 may be in fluid connection to the second end 9004 to determine a pressure of the air in the second opening 9018.

In one form, the port 9032 may be in fluid communication with an interior of the second opening 9018, such as by forming a fluid connection to an opening in the interior of the seal portion 9008. The opening in the interior of the seal portion 9008 may be in turn in fluid communication with a pressure tap 9036 to the second opening 9018. Thus the first end 9002 and the second end 9004 may form two fluid connections therebetween when connected to each other. The port 9032 may provide an advantage of being able to measure pressure closer to a patient than if pressure is measured in the RPT device. Due to pressure losses inherent in internal fluid flow as well as possible leaks throughout the air path from the blower to the patient, measuring the pressure closer to the patient may provide a more accurate measurement than a pressure measurement carried out further from the patient.

Also, the present arrangement allows for the second end 9004 to be rotated with respect to the first end 9002 while still maintaining two fluid connections (i.e. one to deliver the flow of air, another to measure pressure). This may be advantageous for allowing the fluid conduit 9006 to rotate with respect to the outer portion 9026, thus reducing torque imposed on the fluid conduit and/or the outer portion 9026. Furthermore, such a configuration may also allow a user to connect the first end 9002 and the second end 9004 in one of a plurality of rotational orientations to each other while maintaining the two fluid connections.

FIG. 6F illustrates the first end 9002 integrated into an RPT device 4000 with the second end 9004 connected. FIG. 6G illustrates the first end 9002 integrated into the RPT device 4000 with the second end 9004 disconnected.

Although the preceding description generally describes both halves of a connector system together, e.g., a first end 9002 and a second end 9004, it is to be understood that the description of either half may be considered in isolation.

FIGS. 7A-7I illustrate some alternative or additional aspects of the present technology. Except as set forth hereinafter, like reference numbers are the same as described above and thus repetitive description is omitted.

FIG. 7A illustrates the first end 9002 integrated into an RPT device 4000 with the second end connected. FIG. 7B is similar except that the second end 9004 is disconnected, which renders more aspects visible. As best seen in FIG. 7b, the first end 9002 differs from that described above in that a key 9040 and a secondary connector receptacle 9044 are included. The second end 9004 differs in that a slot 9042 and flat 9046 are included. These and other additional features are described in greater detail below.

The keys 9040 and slots 9042 are illustrated on opposed sides (i.e., 180° apart) of the fluid connector 9000. With this orientation, the first end 9002 and second end 9004 may be restricted in that only two mating orientations are possible (e.g., a first orientation and a second orientation where one of the first end 9002 and the second end 9004 is rotated 180° with respect to the other). If two keys 9040 and slots 9042 are provided and separated by an angle less than 180°, then a single mating orientation may be achieved. A single mating orientation may also be achieve by including a single key 9040 and slot 9042. Of course, any number of mating orientations may be achieved by selecting at least the number of slots 9042. For example, by including a single key 9040 and three slots 9042, three different mating orientations can be achieved. As will be appreciated, selecting the number and relative orientation (e.g., angles there between) of keys 9040 and slots 9042, numerous, if not infinite, combinations can be achieved, which may be advantageous in that unique fluid connectors may be achieved while maintaining other common components (such as the seal portion 9008). Of course, the keys 9040 and slots 9042 may be switched, or even intermingled, between the first end 9002 and second end 9004.

The slots and keys may be in one of a number of possible shapes. In one form, the slots and keys may be an elongate shape as for example akin to a mechanical key such as may be used in rotating machinery for alignment and/or retention.

However, a two-orientation configuration as illustrated may be advantageous at least in some scenarios. For example, a two-orientation configuration may allow for easy alignment for the visually impaired or while leaving lights off so as to not disturb a bed partner. If flats 9046 are included on opposed sides where a user would naturally grip the second end 9004 (for example, between a thumb and index finger), the user may readily align the second end 9004 with the first end 9002 by feel. For example, if the first end is included in the RPT device 4000, which as a configuration that allows a user to discern its orientation by feel, both halves of the fluid connector 9000 can be oriented by feel. Of course, the flats 9046 may be omitted and the user may achieve similar effect by grasping the complementary latching portion 9014.

In the particular arrangement shown in FIGS. 7A-7B, the two-orientation configuration may ensure that the cantilevered latching portion is placed angularly displaced (e.g. by 90 degrees) from the electrical connector 9048. As a result, the electrical connector 9048 may be placed directly adjacent to the fluid connector 9000 without adversely affecting access thereto for connection and/or disconnection.

As shown in FIGS. 7C-7D, the inner tube 9022 may extend outwardly to create a cavity in a shape of an annular prism in the first end 9002. The annular cavity may comprise the keys 9040 therein, such as to prevent engagement of other types of connectors that may belong to a component that does not form a part of the intended treatment system. As a result, the user may be prevented from receiving suboptimal therapy, which may result in the user being treated with one or more of: an incorrect pressure, suboptimal flow rates, increased $CO_2$ or others, any of which may result in a suboptimal therapy regime.

Although described herein as flat, the flats 9046 do not necessarily need to be flat in a strict sense. Instead, the flats 9046 may be considered to be less curved or rounded than other portions of the second end 9004 and thus would be more flat or closer to flat than other portions.

The flats 9046 may provide other advantages. For example, as readily seen in FIGS. 7A-7D, a flat 9046 may provide room for or access to a secondary connector receptacle 9046 and/or a main electrical connector 9048. A secondary connector receptacle 9046 may be useful for an electrical connector or fluid connector used in conjunction with the fluid connector 9000. For example, if a version of the fluid conduit 9006 includes electrical components (e.g., a heater and/or a sensor), a flat 9046 may provide room for an electrical connector at the secondary connector receptacle 9044 within the same footprint of the fluid connector 9000 as without the secondary connector 9044. Similarly, if secondary fluid connection is desired (e.g., a pressure sense or fluid sampling line), a similar advantage may be achieved. Of course, a combined fluid and electrical connector could be provided in the secondary connector receptacle 9044. Similar advantages may be provided for the main electrical connector 9048.

Even if the flats 9046 are omitted, it may be advantageous to maintain the same relative orientation as that illustrated because that orientation will orient the complementary latching portions 9014 away from the secondary connector 9044 and electrical connector 9048 (assuming that one or both of those connectors are provided on the RPT device 4000).

FIG. 7N shows a cross-section of a second end 9004 according to another example of the present technology. FIG. 7N shows the outer portion 9026 to comprise an overhang portion 9070. The overhang portion 9070 may extend from approximately an axial position of the sealing surface 9016.

The overhang portion 9070 may be configured such that in use, it would be inserted into an annular cavity in the first end 9002. When engaged with the first end 9002, the overhang portion 9070 may engage an inner surface of the annular cavity to resist relative rotation between the first end 9002 and the second 9004. The distance that overhang portion 9070 extends forwards of the sealing surface 9016 in the axial direction may substantially match the distance that inner tube 9022 and seal portion 9008 extend outwardly from stop 9030 so that, when the end of the overhang portion 9070 abuts stop 9030, the sealing surface 9016 is in sealing contact with seal portion 9008. In this position, sealing portion 9008 may be compressed to ensure a good seal is obtained. The distance that overhang portion 9070 extends forwards may be selected to be a distance that makes it difficult to connect to first end 9002 a second end 9004 that is not specifically designed to connect to first end 9002 to help ensure that only patient interfaces designed to be used with the RPT device are able to be connected thereto.

FIG. 7N also shows the complementary latching portion 9014 to be axially aligned to the sealing surface 9016. For example, an engagement protrusion of the complementary latching portion 9014 may be located axially in line with the sealing surface 9016. The engagement protrusion may comprise a lead-in bevel (as shown in FIG. 7N) to improve ease of insertion of the second end 9004 into the first end 9002.

In some forms the inner portion 9024 may comprise a radial outer surface 9072 configured to engage the inner surface of the complementary latching portion 9014 when depressed. Thus, the radial outer surface 9072 may provide a stop surface configured to limit radial deflection of the complementary latching portion 9014. The radial outer surface 9072 may be axially in line with the sealing surface and/or the engagement protrusion.

As best seen in FIGS. 7E and 7F, the inner portion 9024 includes the sealing surface 9016 at a first end. The inner portion 9024 may be connected to the tube at a second end, such as via an end fitting 9050. The inner portion 9024 may include a stabiliser 9052 that maintains a position of the inner portion 9024 with respect to the outer portion 9026 (FIG. 7I illustrates two stabilisers 9052, FIG. 7N illustrates one stabiliser 9052). The stabiliser 9052 may be made of an elastomer (e.g. a thermoplastic elastomer or silicone) such that it is compliant and resilient. The stabiliser 9052 may be coupled to the inner portion by overmoulding or adhesive. The stabiliser 9052 may thus allow for some movement and tolerances between the inner portion 9024 and outer portion 9026 while maintaining the inner portion 9024 in position with respect to the outer portion 9026 and preventing contact between relatively rigid components which could result in an undesirable rattle sound. The stabiliser 9052 may also include flat portions 9054 (only one visible in FIG. 7f) on diametrically opposed sides to rotationally locate the inner portion 9024 with respect to the outer portion 9026 (e.g. during assembly). The stabiliser 9052 may also be radially tapered, such that the stabiliser 9052 includes thinner wall thicknesses as the radius increases outward.

The outer portion 9026 and/or the inner portion 9024 may comprise or consist of a relatively rigid component, such as polycarbonate or polypropylene. Additionally, the inner surface of the annular cavity of the first end 9002 may further consist of a relatively rigid component. Thus, the engagement between the first end 9002 and the second end 9004 may be made without incurring cumbersome high friction.

In some forms of the technology the outer portion 9026 and inner portion 9024 are discrete components that are connected together during assembly of the second end 9004. This may require manual assembly of the second end 9004 but may have the advantage of that outer portion 9026 and inner portion 9024 are relatively easy to manufacture, e.g. using a moulding process. In alternative forms of the technology, the second end 9004 may be formed by overmoulding inner portion 9024 onto the fluid conduit 9006. One drawback of this approach is that the fluid conduit 9006 and the inner portion 9024 may need to be threaded through the openings in the second end 9004 during assembly.

The stabiliser 9052 may be located towards an end of the inner portion 9024, such as within 5 mm, 10 mm or 15 mm from an end of the inner portion 9024, or 10%, 20%, or 30% of an overall length of inner portion 9024 from one end thereof.

Use of a stabiliser 9052 may more readily allow a reduction in weight of the second end 9004. That is, the inner portion 9024 and the outer portion 9026 may be separated radially by a gap, the size and configuration of which is maintained predictably and stably by the stabiliser 9052. Thus, the assembly of the second end 9004 may reliably form a connection and seal with the first end 9002.

The inner portion 9024 may include a boss 9056 (illustrated as a circumferential shoulder) at the end adjacent the fluid conduit 9006. The boss 9056 may couple with the outer portion 9026. The boss 9056 is located at an opposite end with respect to the stabiliser 9052, such that the inner portion is constrained at two ends. A taper 9058 may be included adjacent the boss 9056. The taper 9058 may ease assembly with the fluid conduit 9006 and/or end fitting 9050.

The outer portion 9026 may include an inner surface on which an overmould 9060 is applied, which may allow relative movement between the complementary latching portion 9014 and surrounding portions of the outer portion 9026. The overmould 9060 may allow for protection against water or other contaminant ingress and prevent or reduce air leakage and/or noise leakage. The overmould 9060 may be provided anywhere that there is a potential ingress or egress path for noise and/or contamination. Other noise reduction features may be provided. For example, a circumferential wall (not illustrated) may be provided radially outward from the seal portion 9008, which may reduce noise leakage through the seal portion 9008.

FIGS. 7G and 7H illustrate a further difference in that engagement between the first end 9002 and second end 9004 is limited by the stop 9030a formed by an end of the slot 9042. Thus the stop 9030 as described above may be omitted. However in some forms of the technology stop 9030 as described above may be present as shown in FIG. 7G. In one embodiment, one or more members formed of a non-rigid material may be mounted to stop 9030. For example, a ring-shaped member or one or more partial ring-shaped members may extend outwards in a radial direction from stop 9030. The ring-shaped members may be made from silicone, for example. Such members mounted to stop 9030 may help to minimise travel of the second end 9004 with respect to the first end 9002 when the two ends are connected and may do so while accommodating manufacturing tolerances. In addition, if the components are configured such that the ring-shaped member(s) need to be compressed in order for latching portion 9012 to engage with complementary latching portion 9014 then this may help provide a more detectable engagement indication (for example an audible and/or tactile click) to a user connecting first end 9002 and second end 9004, which may be desirable to assist a user in knowing when the ends have been connected suitably. Altering the extent to which the ring-shaped members extend outwards from stop 9030 may alter the degree of detectable engagement indication.

FIG. 7J illustrates an alternative configuration to provide a seal between the first end 9002 and the second end 9004, where a conical seal portion 9008a replaces the seal portion 9008 described above. The conical seal portion 9008a contacts and seals with an inner diameter of the stop 9030 instead of the sealing surface 9016.

FIG. 7K illustrates another alternative configuration to provide a seal between the first end 9002 and the second end 9004. Here a flat seal portion 9008b is provided between two flanges 9062a, 9062b.

FIGS. 7L and 7M illustrate another alternative configuration to provide a seal. Here, an exterior (in that it is outside of the flow path) seal is provided by way of an outer conical seal portion 9008c. Such an outer conical seal portion 9008c may contact, and thus seal, on a portion of the housing 9064 of the RPT device 4000 or any other convenient surface outside of the fluid conduit 9006 and/or flow.

A second end 9004 as shown in FIG. 7E (or FIG. 7N) comprises slots 9042, an overhang portion 9070 extending beyond the sealing surface 9016, and an outer profile comprising arcuate portions as well as flat portions. Such combination of features may strongly indicate to the user that the second end 9004 would not be compatible with a standard ISO connector. Thus, advantageously, the user is prevented from setting up the therapy system with sub-optimal components.

FIG. 8A is a perspective view of the seal portion 9008 as discussed above. FIG. 8B illustrates an optional modification of the seal portion 9008 where an inner-most boundary 9066 of the seal portion 9008 is uneven. A roughly sinusoidal boundary is illustrated, but any uneven boundary may be chosen. For example, a sawtooth, square wave, random, or any other non-circular boundary may be chosen. Each of these boundaries may be functionally equivalent. Such uneven boundaries may be beneficial in that a leak is likely to occur if a tube (such as a standard ISO-taper) is inserted into the seal portion 9008. A leak can be detected by the RPT device 4000 and thus the RPT device 4000 could detect when the wrong connection is being used an either issue a warning and/or shut down. Alternatively, the leak could be large enough that the incorrect connection will be rendered non-functional. The leak may be enhanced if the peaks 9066a are relatively more rigid and/or have a higher coefficient of friction than adjacent portions.

FIG. 9 illustrates an alternative leak-inducing feature by way of ribs 9068. The ribs 9068 run under the seal portion 9008 and/or along an interior portion of the flow passage. Such ribs may provide an alternative or additional leak path to that described above, such as when a user attempts to form a seal with an interior of the first tube 9022.

Another way to achieve an intentional leak when attempting to mate one of the first end 9002 and the second end 9004 is to include a second seal that is intended to fully block an opening. For example, the key 9040 could include an elastomeric portion (or any material suitable for sealing), where the elastomeric portion covers and/or seals with a hole in the inner portion 9024. Thus even if a connection is made that adequately seals with the seal portion 9008, a leak would occur that could be detected and cause the RPT device 4000 to react accordingly.

For each of the leak scenarios related to incorrect connections described above, the leaks may be design to provide an audible warning to a user. Thus instead of or in addition to the RPT device 4000 reacting to the leak, a user may be provided with an audible indication that the wrong connection is being used.

Another feature to reduce the likelihood of an incorrect connection being made is to extend the pressure tap 9036 into the center of the flow path similar to a pitot tube. This may partially occlude the flow path such that a tube cannot be inserted far enough to form a seal. Alternatively, the pressure tap 9036 may be blocked, which could be detected by the RPT device 4000.

4.7 GLOSSARY

For the purposes of the present technology disclosure, in certain forms of the present technology, one or more of the following definitions may apply. In other forms of the present technology, alternative definitions may apply.

4.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Continuous Positive Airway Pressure (CPAP) therapy: CPAP therapy will be taken to mean the application of a supply of air to an entrance to the airways at a pressure that is continuously positive with respect to atmosphere. The pressure may be approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Patient: A person, whether or not they are suffering from a respiratory disease.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Vent: (noun) the structure that allows an intentional flow of air from an interior of the mask, or conduit to ambient air, e.g. to allow washout of exhaled gases.

4.7.2 Aspects of the Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

4.7.3 RPT Device Parameters

Flow rate: The instantaneous volume (or mass) of air delivered per unit time. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Flow rate will be given the symbol Q. 'Flow rate' is sometimes shortened to simply 'flow'. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system. Respiratory flow rate, Qr, is the flow rate of air that is received into the patient's respiratory system.

Leak: The word leak will be taken to be an unintended flow of air. In one example, leak may occur as the result of an incomplete seal between a mask and a patient's face. In another example leak may occur in a swivel elbow to the ambient.

4.7.4 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240

Polycarbonate: a typically transparent thermoplastic polymer of Bisphenol-A Carbonate.

4.8 OTHER REMARKS

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

4.9 REFERENCE SIGNS LIST 1000 patient
1100 bed partner
3000 patient interface
3100 seal-forming portion
3110 sealing flange
3120 support flange
3200 plenum chamber
3210 perimeter
3220 marginal edge
3300 structure
3400 vent
3500 decoupling structure
3510 swivel
3520 socket
3600 connection port
3700 forehead support
3800 anti-asphyxia valve
4000 rpt device
4010 external housing
4012 upper portion
4014 portion
4015 panel
4016 chassi
4018 handle
4020 pneumatic block
4100 pneumatic component
4110 air filter
4112 inlet air filter
4114 outlet air filter
4122 inlet muffler
4124 outlet muffler
4140 pressure generator
4142 blower
4144 motor
4170 air circuit
4180 supplemental oxygen
4200 electrical component
4202 board Assembly PCBA
4210 power supply
4220 input device
4230 central controller
4232 clock
4240 therapy device controller
4250 protection circuit
4260 memory
4270 transducer
4272 pressure transducer
4272 pressure sensor
4274 flow rate sensor
4276 motor speed transducer
4280 data communication interface
4282 remote external communication network
4284 local external communication network
4286 remote external device
4288 local external device
4290 output device
4292 display driver
4294 display
4300 algorithm
4310 pre-processing module
4312 pressure compensation algorithm
4314 vent flow rate calculation algorithm
4316 leak flow rate algorithm
4318 respiratory flow rate algorithm
4320 therapy engine module
4321 phase determination algorithm
4321 fuzzy phase determination algorithm
4322 waveform determination algorithm
4323 ventilation determination algorithm
4324 inspiratory flow limitation determination
4325 apnea/hypopnea determination
4326 snore determination algorithm
4327 airway patency determination algorithm
4328 target ventilation determination algorithm
4329 therapy parameter determination algorithm
4330 therapy control module
5000 humidifier
5250 humidifier controller
9000 fluid connector
9002 first end
9004 second end
9006 fluid conduit
9008 seal portion
9008a conical seal portion
9008b flat seal portion
9008c outer conical seal portion
9010 first opening
9012 latching portion
9014 complementary latching portion
9016 sealing surface
9018 second opening
9020 second tube
9022 first tube
9024 inner portion
9026 outer portion
9028 interface
9030 stop 9030a stop
9032 port
9034 overhang portion
9036 pressure tap
9038 guide portion
9040 key
9042 slot
9044 secondary connector receptacle
9046 flat
9048 main electrical connector
9050 end fitting
9052 stabiliser
9054 flat portion
9056 boss
9058 taper
9060 overmould
9062a flange
9062b flange
9064 housing
9066 inner-most boundary
9066a peak
9068 rib
9070 overhang portion

The invention claimed is:

1. A fluid connector system for delivery of breathing gas to a patient from a respiratory pressure therapy device, the fluid connector system comprising:
a first end portion with a first opening for a fluid flow, a seal portion extending around a periphery of the first opening, and a latching portion, and
a second end portion with an inner tube defining a second opening for the fluid flow, a sealing surface extending around a periphery of the second opening and configured to engage the seal portion to form a face seal, and an outer tube comprising a complementary latching portion configured to engage with the latching portion and configured to be depressed into a cavity formed between the inner tube and the outer tube,
wherein the face seal forms a seal to breathing gas travelling between the first opening and the second opening, and the engagement between the latching portion and the complementary latching portion secures the first end portion with the second end portion,
wherein, when the first end portion and the second end portion are connected, the seal portion is configured to engage the sealing surface before the latching portion and the complementary latching portion touch,
wherein the seal portion includes a bellows-shape, a partial bellows shape, or a frustoconical portion, and
wherein the bellows-shape, partial bellows shape, or frustoconical portion contacts the sealing surface to form the face seal when the first end portion and the second end portion are connected.

2. The fluid connector system according to claim 1, wherein the second end portion further comprises a stabiliser located between the inner tube and the outer tube.

3. The fluid connector system according to claim 2, wherein the stabiliser is formed at least in part from an elastomer.

4. The fluid connector system according to claim 1, wherein the first end portion is connected to a respiratory pressure therapy device including a blower and the second end portion is connected to a fluid conduit.

5. The fluid connector system according to claim 1, wherein the sealing surface is flat.

6. The fluid connector system according to claim 5, wherein the sealing surface is substantially perpendicular to a direction of the fluid flow from the first end portion to the second end portion.

7. The fluid connector system according to claim 1, wherein the sealing surface extends circumferentially around the second opening.

8. The fluid connector system according to claim 1, wherein the sealing surface is formed on a flange that extends radially from the inner tube.

9. The fluid connector system according to claim 8, wherein the flange extends substantially perpendicularly from the inner tube.

10. The fluid connector system according to claim 8, wherein the inner tube extends beyond the flange in a direction towards the seal portion.

11. The fluid connector system according to claim 10, wherein the inner tube extends at least partially though the seal portion when the complementary latching portion is engaged with the latching portion.

12. The fluid connector system according to claim 1, wherein the seal portion is compliant in a direction of engagement between the first end portion and the second end portion.

13. The fluid connector system according to claim 1, wherein the seal portion includes the frustoconical portion.

14. The fluid connector system according to claim 13, wherein the frustoconical portion contacts the sealing surface to form the face seal when the first end portion and the second end portion are connected.

15. The fluid connector system according to claim 1, wherein the seal portion includes a partial spherical surface.

16. The fluid connector system according to claim 15, wherein the partial spherical surface contacts the sealing surface to form the face seal when the first end portion and the second end portion are connected.

17. The fluid connector system according to claim 1, wherein the seal portion includes flail the bellows-shaped or partial bellows-shaped portion.

18. The fluid connector system according to claim 17, wherein the bellows-shaped or partial bellows-shaped portion contacts the sealing surface to form the face seal when the first end portion and the second end portion are connected.

19. The fluid connector system according to claim 1, wherein the seal portion is compliant in a direction radial to an axis defined by a direction of engagement between the first end portion and the second end portion.

20. The fluid connector system according to claim 1, wherein the seal portion is formed as a cantilever structure having a fixed end proximate to the first opening and a free end projecting away from the fixed end, the fixed end being fixedly mounted on the first end portion, and the free end configured to engage the sealing surface in order to form the face seal.

21. The fluid connector system according to claim 1, wherein the seal portion includes a substantially circular profile, and wherein an inner diameter of the seal portion decreases along an axial direction away from the first opening.

22. The fluid connector system according to claim 1, wherein the seal portion at least partially forms a seal opening separate from the first opening.

23. The fluid connector system according to claim 22, wherein the seal opening and the first opening are concentric and axially spaced from one another.

24. The fluid connector system according to claim 1, wherein the second end portion further includes an overhang that extends beyond the sealing surface, the seal portion configured to engage the second end portion proximate to a corner formed between the overhang and the sealing surface, wherein the overhang prevents the sealing surface from extending into the first opening or the second opening when the second end portion is coupled to the first end portion, and wherein the overhang is configured to contact a stop of the first end portion in order to limit travel of the second end portion into the first opening.

* * * * *